US006486166B1

(12) United States Patent
Albrecht et al.

(10) Patent No.: US 6,486,166 B1
(45) Date of Patent: Nov. 26, 2002

(54) SUPPRESSION OF CYCLIN KINASE 2 ACTIVITY FOR PREVENTION AND TREATMENT OF DNA VIRAL INFECTIONS

(75) Inventors: Thomas Albrecht, Galveston, TX (US); Aubrey E. Thompson, Dickinson, TX (US); Wade Bresnahan, Plainsboro, NJ (US); Laurent Meijer, Roscoff (FR)

(73) Assignee: Board of Regents, The University of Texas, Austin, TX (US)

( * ) Notice: Subject to any disclaimer, the term of this patent is extended or adjusted under 35 U.S.C. 154(b) by 0 days.

(21) Appl. No.: 09/389,830

(22) Filed: Sep. 3, 1999

Related U.S. Application Data

(63) Continuation of application No. PCT/US98/04154, filed on Mar. 2, 1998.
(60) Provisional application No. 60/038,126, filed on Mar. 3, 1997, now abandoned.

(51) Int. Cl.$^7$ .......................... A61K 31/52; A61P 31/20
(52) U.S. Cl. ................... 514/261; 514/844; 514/934; 514/824
(58) Field of Search ................. 514/261, 931, 514/934, 824, 894

(56) References Cited

FOREIGN PATENT DOCUMENTS

WO    WO 97/20842    6/1997

OTHER PUBLICATIONS

Bresnahan et al., "Inhibition of cellular cdk2 activity blocks human cytomegalovirus replication," *Virology*, 231:239–247, 1997.

Meijer et al., "Biochemical and cellular effects of roscovitine, a potent and selective inhibitor of the cyclin–dependent kinases cdc2, cdk2 and cdk 5," *Eur. J. Biochem.*, 243:527–536, 1997.

Vesely et al., "Inhibition of cyclin–dependent kinases by purine analogues", *Eur. J. Biochem.*, 224:771–786, 1994.

Bresnahan et al., "Human cytomegalovirus inhibits cellular DNA synthesis and arrests productively infected cells in late G1," Abstract, *Virology*, 224(1):150–160, 1996.

De Azevedo et al., "Inhibition of cyclin–dependent kinases by purine analogues: crystal structure of human cdk2 complexed with roscovitine," *Eur. J. Biochem.*, 243(1/2):518–526, 1997.

Schulze–Gahmen et al., "Multiple modes of ligand recognition: crystal structures of cyclin–dependant protein kinase 2 in complex with ATP and two inhibitors, olomoucine and isopentenyladine," *Proteins: Structure, Function and Genetics*, 22:378–391, 1995.

Abraham et al., "Cellular effects of olomoucine, and inhibitor of cyclin–dependant kinases," Abstract, *Biol. Cell*, 83(2–3:105–120, 1995.

*Primary Examiner*—Edward J. Webman
(74) *Attorney, Agent, or Firm*—Fulbright & Jaworski

(57) ABSTRACT

An important aspect of the present invention is a method for inhibiting proliferation of a DNA virus dependent upon events associated with cell proliferation for replication. The DNA virus includes any of the herpesvirus family, and most particularly human cytomegalovirus. The method involves administering prophylactically or therapeutically effective amount of a cyclin-dependent kinase inhibitor to a patient or animal.

27 Claims, 18 Drawing Sheets

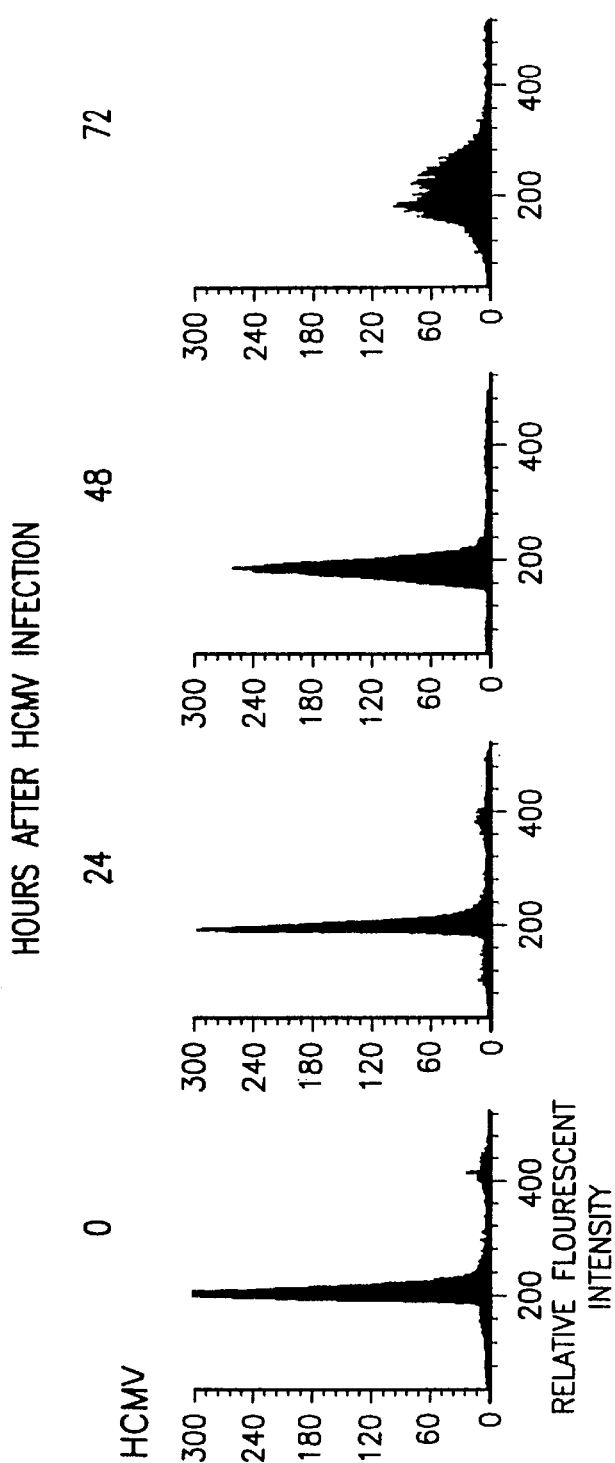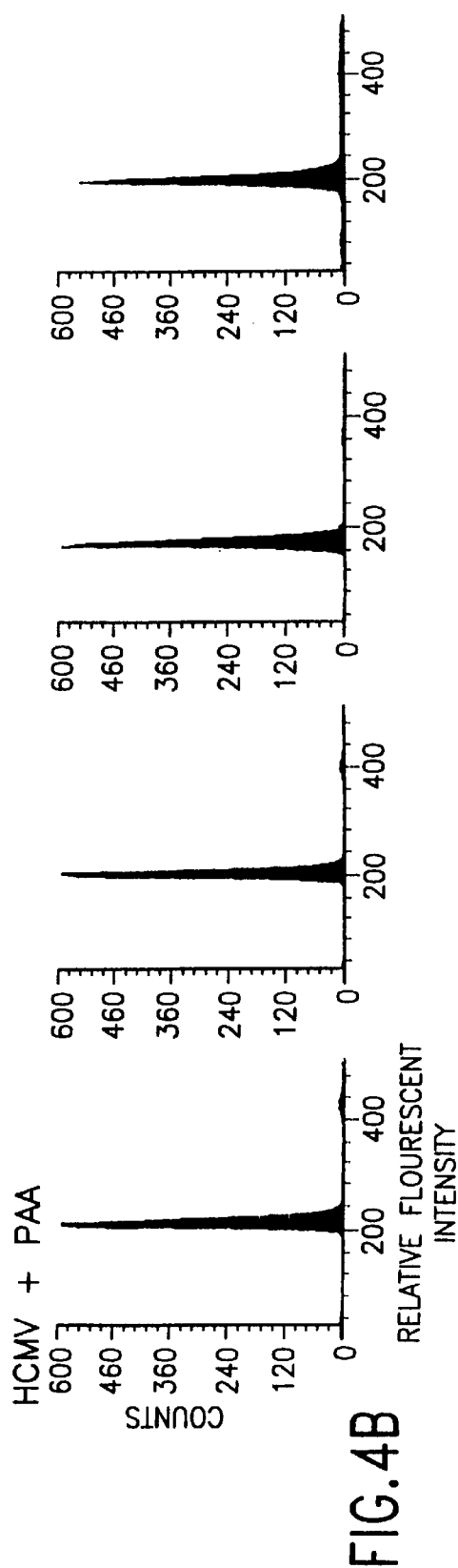
FIG.4A
FIG.4B

HEMATOXYLIN AND EOSIN STAINING

96 HR IN 15μM ROSCOVITINE

96 HR P.I. 0μM ROSCOVITINE

96 HR P.I. 5μM ROSCOVITINE

96 HR P.I. 15μM ROSCOVITINE

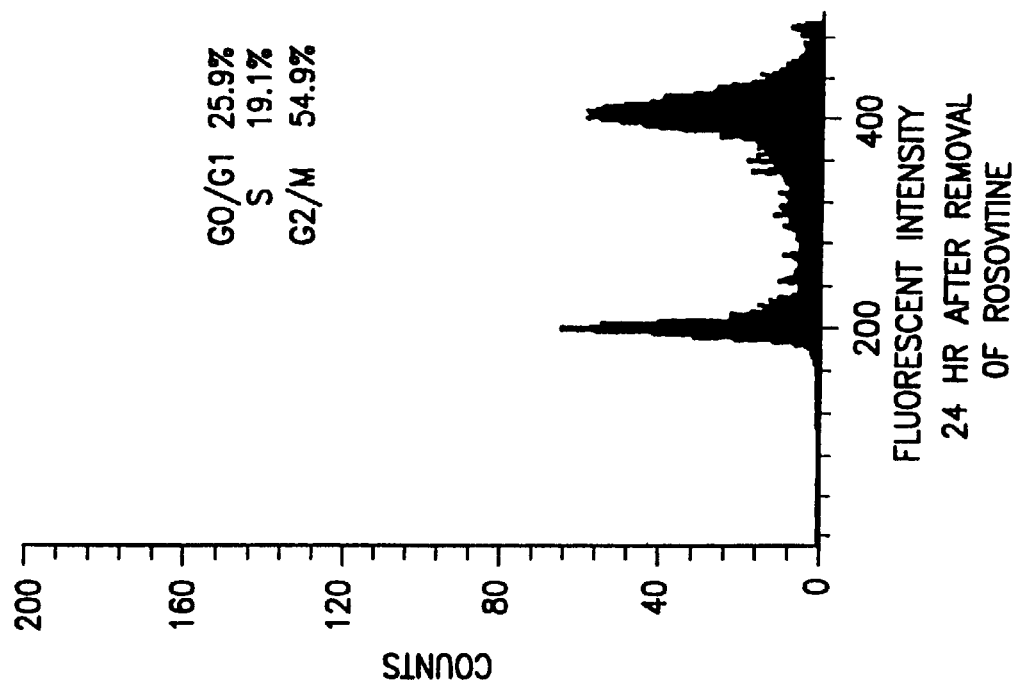
FIG.11A2
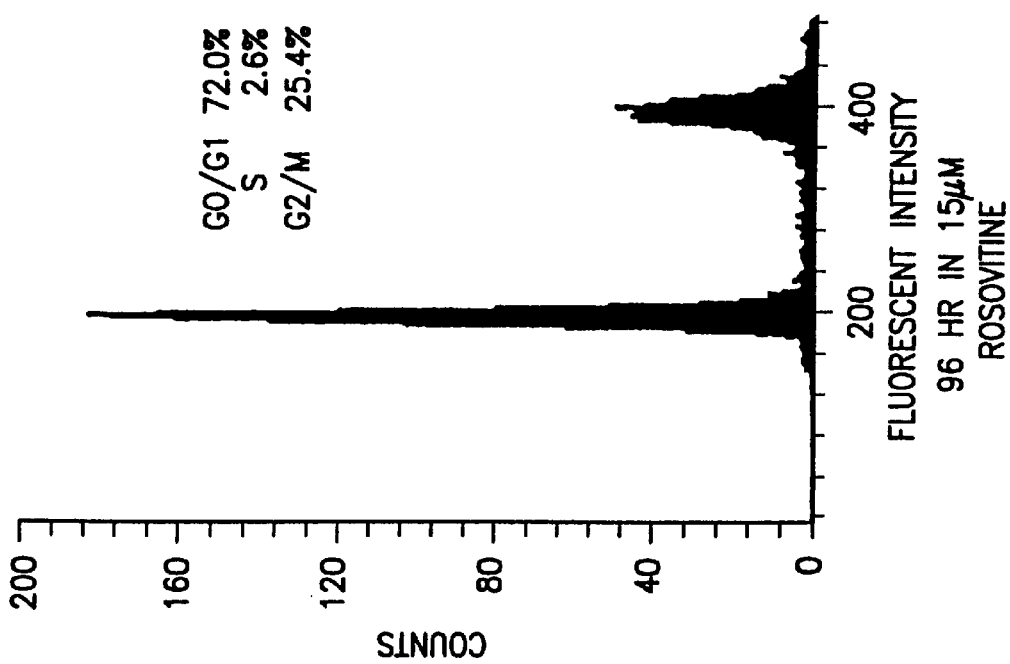
FIG.11A1

SUPPRESSION OF CYCLIN KINASE 2 ACTIVITY FOR PREVENTION AND TREATMENT OF DNA VIRAL INFECTIONS

This is a continuation of co-pending international application number PCT/US98/04154 filed Mar. 2, 1998, which is a continuation-in-part of U.S. provisional patent application Ser. No. 60/038,126 filed Mar. 3, 1597, now abandoned.

BACKGROUND OF THE INVENTION

The entire text of the above-referenced disclosure is specifically incorporated by reference herein without disclaimer.

The present invention relates generally to the fields of prophylaxis and treatment for viral infections. More particularly, it concerns the use of cyclin dependent kinase inhibitors for blocking replication of any DNA virus dependent on Cdk activity for proliferation, an example being herpesvirus and, more particularly, cytomegalovirus. Marek's disease represents a chicken-CMV, equine abortion virus represents a horse variety and cattle have several specific CMV's, to name but a few species-specific CMV's.

Human cytomegalovirus (HCMV) is a ubiquitous herpesvirus that infects greater than 80% of the human population. HCMV is capable of establishing a life-long infection following primary infection. Reactivation of HCMV often results during pregnancy, perfusion, and in immunocompromised states (Huang and Kowalik, 1993). HCMV rarely causes symptomatic disease in healthy immunocompetent individuals. However, HCMV can result in severe clinical manifestations in congenitally infected newborns and in immunocompromised individuals, such as those undergoing organ transplantation or those infected with HIV (Alford et al., 1990; Schooley, 1990; Rubin, 1990). Most animal species may be infected with species-specific cytomegalovirus.

HCMV is the most common cause of human congenital viral infections, occurring in approximately 1% of all new born infants (Weller, 1971; Alford et al., 1981). Congenital infections (e.g., those acquired during pregnancy) primarily result from reactivation of a latent infection in the mother and subsequent transmission to the fetus. The majority of HCMV infections are asymptomatic or subclinical. However, about 10% of infants infected in utero display clinical manifestations, approximately 5% display typical cytomegalic inclusion disease (CID), with the other 5% presenting atypical manifestations (Pass et al., 1980). Characteristic manifestations of CID include hepatomegaly, splenomegaly, microcephaly, jaundice, and petechiae (Weller and Hanshaw, 1964). The prognosis for congenital CID is bleak with the mortality rate reaching 30%. The surviving infants may suffer from severe mental and motor abnormalities (Alford et al., 1990).

Perinatal infections are acquired during or shortly after birth. It is estimated that 1 to 15% of infants born in the United States become infected with HCMV by 6 months of age (Alford et al., 1990). The majority of these, infections occur via ingestion of infected breast milk and contact with genital secretions during birth. Approximately 40–60% of infants breast-fed by sero-positive mothers and 25–50% of infants exposed to HCMV in the birth canal become infected (Stagno et al., 1980; Dworsky et al., 1983; Reynolds et al., 1973). The vast majority of these perinatal infections remain asymptomatic. However, there is evidence that perinatal HCMV infection may be associated with interstitial pneurmonitis and result in chronic lung disease (Brasfield et al, 1987).

HCMV's ability to latently infect cells and become reactivated under immunosuppressed conditions pose a severe problem for AIDS patients (Chou, 1990; Drew et al., 1981; Quinn et al., 1987). Essentially 100% of HIV positive homosexual men present serological evidence of either recently acquired or reactivated HCMV infection (Collier et al,. 1987). According to Schooley (1990), HCMV can play at least four possible roles in the pathogenesis of AIDS. These include: 1) direct HCMV-induced morbidity associated with clinical symptoms, 2) increased immunosuppression induced by HIV, 3) enhanced HIV replication by trans-activation at the cellular level, and 4) destruction of the gastrointestinal mucosa, and predisposition to other infections.

HCMV infection is the primary cause of death in over 35% of AIDS patients (Gehrz, 1991). HCMV infection affects numerous organ systems including the central nervous system (CNS), pulmonary system, and gastrointestinal (GI) tract (Smith and. Brunnessel, 1994). HCMV infection of the CNS has been observed in more than 20% of AIDS patients at autopsy. Individuals with CNS infections present with clinically recognized neurological symptoms including encephalitis, polyradiculomyelitis, and neuropathy (Navia et al., 1986; Hawley et al., 1983; Said et al., 1991). It is estimated that ~20% of AIDS patients will develop a gastrointestinal disease caused by HCMV (Dieterich et al., 1993). HCMV infection can result in lesions involving the oral mucosa, esophagus, intestine, and rectum (Kanas et al., 1987). The pain associated with these lesions of the GI tract can obstruct the intake of food and thus contribute to the already poor nutritional status of the patient (Villor et al., 1984).

HCMV also affects the immunological state of AIDS patients. HCMV induces numerous immunological abnormalities that can inhibit the patients ability to fight HIV and other infections. These abnormalities include; changes in the relative distribution of CD4 and CD8 T-lymphocytes (Drew et al., 1985; Detels et al., 1984), a decrease in release of and responsiveness to mitogens, (Kapasi and Rice, 1988; Sing and Garnett, 1984) altered HLA-DR expression, and altered antigen presentation (Fiala et al., 1993).

Interestingly, HCMV may also enhance HIV replication at a molecular level. Previous studies have demonstrated that HCMV and HIV can co-infect numerous cell types (Rice et al., 1984; Nelson et al., 1988). This coinfection of HCMV and HIV can result in the enhancement of HIV replication via the trans-activation of the long terminal repeat (LTR) sequences by HCMV regulatory elements (Schooley, 1990). Although the complete mechanism is far from clear, the net result is enhanced expression of the LTR and increased HIV replication.

A second group of individuals with increased risk of HCMV infection are organ transplant recipients. HCMV is the single most important infectious agent affecting organ recipients. At least two-thirds of these patients develop a HCMV-infection 1–4 months after transplantation (Rubin, 1990). According to Rubin (1990) there are three patterns of HCMV infection following organ transplantation; primary infection, reactivated infection, and superinfection. Primary infection has the greatest clinical impact and occurs when an individual who is sero-negative for HCMV becomes infected by a sero-positive donor organ or transfused blood. In reactivated infection the HCMV sero-positive recipient undergoes reactivation of endogenous latent virus. Virtually all organ recipients who are scro-positive for HCMV will show some evidence of HCMV reactivation (Rubin and Tolkoff-Rubin, 1984; Fiala et al., 1975). Finally, superinfection occurs when a sero-positive recipient receives an allograft from a sero-positive donor that is infected with a different HCMV strain.

HCMV-infection itself can result in a wide variety of conditions ranging from fevers to pneumonia and hepatitis (Rubin, 1990). Secondly, HCMV infection can produce an immunosuppressed state that exceeds that observed from the immunosuppressive drugs alone. This enhanced immunosuppression can result in increased opportunistic infections due to *Pneumocystis carinii*, fungi, and *Listeria monocytogenes* (Rubin, 1990). Finally, HCMV can directly contribute to the rejection of the allograft. These complications demonstrate the need to better understand the HCMV life cycle. Understanding the molecular mechanisms of HCMV replication should aid in the development of novel anti-virals to help control the spread and replication of HCMV.

The structure of the HCMV virion shares characteristics consistent with other DNA viruses, particularly the herpesviruses. The HCMV virion consists of four basic elements: 1) an electron-opaque core, 2) an icosahedral capsid surrounding the core, 3) a tegument surrounding the capsid, and 4) an envelope (Roizmnan and Sears, 1991).

HCMV gene expression is regulated by a complex interaction of both viral and cellular proteins (Huang and Kowalik, 1993). The most complex and well studied HCMV regulatory element is the major immediate early promoter (MIEP) which promotes transcription of the immediate early genes. The MIEP is an extremely strong and complex promoter containing numerous binding sites for cellular transcription factors that regulate IE gene expression (Boshart et al., 1985; Samnbuchetti et al., 1989). The MIEP contains various 17,18, 19, and 21 base pair repeats upstream of the transcriptional start site for IE1 and IE2. These repeats contain binding sites for cellular transcription factors such as NFκB, SP1, NF1, and ATF/CREB. Other cis elements located outside the repeat elements include a serum-response element (SRE), glucocorticoid-response element (GRE), and AP-1 binding sites (reviewed in Huang and Kowalik, 1993). All of these cis-elements are thought to play important roles in regulating transcription from the MIEP. However, HCMV gene expression is not controlled exclusively by cellular transcription factors. The major immediate early proteins also play critical roles in regulating the MIEP. IE72 and 55 can upregulate transcription from the MIEP (Cherrington and Mocarski, 1989; Stenberg et al., 1990; Baracchini et al., 1992), whereas IE86 represses transcription from the MIEP (Stenberg et al., 1990). This repression by IE86 presumably occurs by direct or indirect interaction with a cis-repression signal in the MIEP that spans the transcriptional start site (Cherrington et al., 1991; Liu et al., 1991). Control of the MIEP by IE72, 55, and 86, is believed to provide an intermediate level of promoter activity necessary for maintaining proper levels of IE proteins for subsequent viral and cellular gene activation (Stenberg et al., 1990). HCMV early and late promoters are also regulated by IE proteins (Malone et al., 1990; Staprans et al., 1988). However, these promoters require both IE72 and IE86, along with cellular transcription factors for maximal expression (Chang et al., 1989; Depto and Stenberg, 1989; Malone et al., 1990). An example of this regulation occurs in transcription of the HCMV DNA polymerase gene. Transcription of the polymerase gene requires both IE72 and IE86 proteins together with the cellular transcription factor USF for promoter activity (Klucher et al., 1989). Immediate early proteins are also involved in activating cellular promoters. Recent studies have demonstrated HCMV's ability to activate cellular genes such as, dihydrofolate reductase (Margolis et al., 1995), thymidine kinase (Estes and Huang, 1977), and topoisomerase II (Benson and Huang, 1990). Some of these promoters are regulated by interaction of IE proteins and cellular transcription factors (Margolis et al., 1995). The ability of HCMV to induce transcription and expression of these cellular genes is believed to be critical for successful viral replication.

The time required for maximal HCMV DNA synthesis is quite long compared to other herpesviruses. HCMV encodes its own DNA polymerase which is responsible for the synthesis of viral DNA. The HCMV DNA polymerase is a 140 kDa protein that possesses 3' exonuclease activity (Huang, 1975a; Nishiyama et al., 1983). The HCMV polymerase is structurally and functionally distinct from cellular DNA polymerases and can be specifically inhibited by chemicals such as phosphonoacetic acid (Huang, 1975b).

HCMV DNA synthesis appears to occur in a biphasic manner, with synthesis beginning approximately 12 hrs post-infection. The first phase of synthesis slows at about 24 hr post-infection (Albrecht, 1989; Stinski, 1978). Maximum viral DNA synthesis, however, does not occur until 72–96 hr post-infection (Albrecht. 1989; Stinski, 1978). The reason for this slow rate of viral DNA synthesis is presently unknown. Some researchers have speculated that since HCMV stimulates host cell macromolecular synthesis, that at early times after infection when macromolecules are limiting, HCMV does not compete well with the host cell for these factor (Stinski, 1991). According to this hypothesis, the virus must first induce synthesis of macromolecules (i.e., nucleotides) before efficient viral DNA synthesis can occur.

The early events that one observes upon HCMV infection share many aspects in common with the cellular immediate early response that is provoked by addition of serum growth factors to serum-starved cells. The virus precipitates a very rapid increase in the intracellular concentration of many important second messengers (reviewed in Albrecht et al, 1989), including calcium, inositol trisphosphate, and diacylglycerol. Protein kinase C, along with phospholipase A2 are also activated following infection (AbuBakar et al., 1990). HCMV infection also induces dramatic changes in Na+/IK+ ATPase activity following infection (Albrecht et al., 1989). Albrecht (1989) has proposed that these changes in second messengers and intracellular ions are crucial for the morphological and pathological responses observed following HCMV infection.

HCMV replication in vivo occurs in terminally differentiated cells of epithelial and endothelial origin (Weller, 1971). Therefore, successful viral replication requires activation of the DNA synthetic machinery, as well as those pathways that are involved in biosynthesis of macromolecular precursors (nucleotides, polyamines, etc.). These processes are stringently repressed in post-mitotic cells. However, HCMV is capable of overcoming these restrictions to allow for viral replication. HCMV infection is capable of inducing numerous cellular genes involved in production of biosynthetic precursors and genes involved in transcriptional regulation. The expression of cellular immediate early genes such as c-fos, c-jun, and c-myc, all of which can act as transcription factors, are increased following HCMV infection (Boldogh et al., 1990; Monick et al., 1992; Colberg-Poley and Santomenna, 1988). Biosynthetic genes involved in nucleotide production such as dihydrofolate reductase, thymidine kinase, and ornithine decarboxylase are also induced following HCMV infection (Margolis et al., 1995; Estes and Huang, 1977; Isom, 1979). The induction of these genes demonstrates HCMV's ability to overcome some of the restrains present in post-mitotic cells and induce the production of precursors required for HCMV replication.

It is generally agreed that in some cell types HCMV is capable of evoking a complete mitogenic response leading to replication of the host cell genome. (Albrecht et al., 1976; DeMarchi, 1983; Fumkawa et al., 1975; Kamiya et al., 1986). However, many (perhaps all) of these cells that exhibit a complete mitogenic response upon viral infection do not replicate the viral genome and fail to produce progeny virus (Albrecht et al., 1976; DeMarchi, 1983; Albrecht et al., 1989). The data suggest that failure to express the full complement of viral genes needed for HCMV replication may permit host cell DNA replication, such that a complete mitogenic response appears to be characteristic of cells that undergo abortive infection.

In cells that produce virus progeny (i.e., during productive infection), there is controversy concerning the extent to which the virus is capable of activating host cell DNA synthesis. It is clear that productively infected cells exhibit many manifestations of mitogenic stimulation (Albrecht et al., 1989; Yurochko et al., 1995; Bresnahan et al., 1996a; Wade et al., 1992; Estes and Huang, 1977; Jault et al., 1995). Some investigators have reported that complete (or nearly complete) replication of the cellular genome attends HCMV DNA synthesis in productively infected cells (Jault et al., 1995; St. Jeor and Hutt, 1977), leading to arrest of infected cells in a state that resembles G2 or M phase of the cell cycle (Jault et al., 1995). Other investigators have been unable to detect cellular DNA synthesis in cells that are replicating HCMV DNA and producing virus progeny (De Marchi, 1983; Albrecht et al., 1989, Bresnahan et al., 1996a). Thus, it is unclear to what extent HCMV is capable of eliciting a complete mitogenic response, leading to activation of the cellular DNA synthetic machinery and a significant increase in host cell DNA synthesis during the course of productive viral replication. Neither is it certain how the virus subverts the normal, post-mitotic constraints on DNA synthesis and biosynthesis of macromolecular precursors.

The ability of HCMV to activate cells is an important step in HCMV replication. However, the controversy of whether or not HCMV elicits a complete mitogenic signal and stimulates cellular DNA synthesis is ongoing. The cell cycle is divided into four distinct phases referred to as G1, S, G2 and M phase. These four phases encompass distinct molecular events that direct cell division. DNA synthesis and replication of the cellular genome occurs in S phase. The molecular events involved in chromosome separation and the formation of daughter cells occurs in M phase or mitosis (reviewed in Alberts et al., 1989). Gap 1 or G1 occurs after mitosis (cell division) and prior to the initiation of S phase. It is during this G1 phase that the cell will make a decision either to become quiescent or commit to another round of DNA replication (reviewed in Draetta, 1994; Sherr, 1994). Gap 2 or G2 represents the time between S phase and the initiation of mitosis (Alberts et al., 1989). Recent studies have begun to elucidate the mechanisms involved in regulating progression through each of these phases. These mechanisms are crucial for faithful replication of the genome and successful cell proliferation. Although the picture is far from clear some key genes regulating cell cycle progression have been identified.

Progression through the eukaryotic cell cycle is regulated by a family of serine/threonine protein kinases called cyclin-dependent kinases or Cdks (reviewed in Draetta, 1994; Sherr, 1993; Sherr, 1994). The activity of Cdks are closely regulated by numerous mechanisms some of which include, specific binding to regulatory subunits, called cyclins, binding to inhibitory subunits called cyclin kinase inhibitors (CKIs), phosphorylation, dephosphorylation, and protein degradation (reviewed in Elledge and Harper, 1994; Morgan, 1995; Sherr, 1994). The temporal activation and binding of cyclins to specific Cdks is shown in FIG. 1. The regulation and activity of Cdks is essential for successful cell cycle progression and cell proliferation.

Cdks comprise a family of at least 10–12 enzymes. Some of these enzymes have been studied in considerable detail. The first Cdk was identified in fission and budding yeast and designated cdc2 and cdc28, respectively (Nurse and Bissett, 1981; Lorincz and Reed, 1984). Cdk1 is the metazoan homologue of cdc2 and cdc28 (Hanks, 1987). Cdk1 complexes with both cyclins A and B and plays a critical role in regulating the G2/M phase transition (Sherr, 1983; Draetta, 1994). Cdk3 has been implicated in progression through G1 phase of the cell cycle (van den Heuvel and Harlow, 1993), but little more is known of this enzyme. Cdk5 functions in neural tissues (Lew et al., 1994). Cdk7 is the catalytic subunit of the Cdk activating kinase (CAK), which as the name implies, plays a role in regulating Cdk activity (Fesquet et al., 1993; Fisher and Morgan, 1994). Cdk2, Cdk4, and Cdk6 are thought to play critical roles in G1 phase progression. The precise details are far from clear, but it is generally believed that Cdk4 and Cdk6 regulate processes that are essential for progression through mid to late G1 phase; whereas Cdk2 regulates processes that are involved in the initiation of S phase (reviewed in Draetta, 1994; Sherr, 1993; Sherr, 1994). Cdk4 and Cdk6 are activated by association with one or another of the D-type (D1, D2, D3) cyclins (Bates et al., 1994; Matsushime et al., 1992; Meyerson and Harlow, 1994). Cdk2 is activated primarily by association with cyclin E or cyclin A (Dulic et al., 1992; Koff et al., 1992; Rosenblatt et al., 1992).

The biochemical consequences of cyclin binding to Cdks are not well understood, although it is known that binding of cyclins is a prerequisite for covalent modifications that are essential for catalytic activity (reviewed in Clarke, 1995; Morgan, 1995). For example, binding of an appropriate cyclin is required in order for Cdk-activating kinase (CAK) to phosphorylate T160 on Cdk2 and T174 on Cdk4 (Gu et al., 1993; Kato et a., 1994). The Cdks are inactive unless these carboxy-terminal threonine residues are phosphorylated. Cyclin kinase inhibitors act in part to block CAK-dependent activation of Cdks (Gu et al., 1993; Kato et al., 1994; Slingerland et al., 1994), suggesting that cyclins and CKIs serve antagonistic functions with respect to CAK-dependent activation of Cdks.

Broadly speaking, there are two classes of metazoan CKIs. One class consists of the members of the INK family, which include but is probably not limited to p15, p 16, p18, and p19 (reviewed in Elledge and Harper, 1994; Hunter and Pines, 1994; Sherr and Roberts, 1995). INK type CKIs bind to and sequester Cdk4 and Cdk6, but not Cdk2. The sequestration of the Cdk subunit by these inhibitors prevents Cdk4 or 6 from complexing with its cyclin subunit (Serrano et al., 1993; Hannon and Beach, 1994). The INK type inhibitors also prevent Cdk4 and Cdk6 phosphorylation by dissociating the cyclin/Cdk binary complex which is the substrate for CAK. Activated cyclinD/Cdk4 complexes (i.e., those in which T174 has already been phosphorylated) are also inhibited due to displacement of the cyclin subunit by these inhibitors (reviewed in Elledge and Harper, 1994; Hunter and Pines, 1994; Sherr and Roberts, 1995).

The second family of CKIs, is comprised of Cip1 (also called WAF1, Cap20, and Sdi1) Kip1 and Kip2 (Harper et al., 1993; El-Deiry et al., 1993; Polyak et al., 1994; Toyoshima and Hunter, 1994). These CKIs bind to cyclin/Cdk binary complexes that contain Cdk2, Cdk3, Cdk4, or Cdk6 (reviewed in Elledge and Haper, 1994; Hunter and Pines, 1994; Sherr and Roberts, 1995). Unlike members of the INK family, Cip1 and Kip1 do not disrupt cyclin/Cdk complexes, but bind to such entities to form ternary and higher order complexes (Harper et al., 1993; Harper et al., 1995; Xiong et al., 1992, Zhang et al., 1993). Cip 1 and Kip1 are structurally related to each other, but not to the INK-type CKIs (Hannon and Beach, 1994; Polyak et al., 1994; Serrano et al., 1993; Toyoshima and Hunter, 1994). Both Cip1 and Kip1 have similar properties in vitro. Both inhibit phosphorylation by CAK at low stoichiometries, thereby preventing Cdk activation (Gu et al, 1993; Harper et al., 1993; Polyak et al., 1994; Toyoshima and Hunter, 1994). Cip1 appears to facilitate the formation of cyclin A/Cdk2 complexes at low concentrations of the inhibitor (Haper et al., 1995; Zhang et al., 1994), and it has been suggested that Cip1 may be involved in recruitment of cyclin A and Cdk2 to newly synthesized ternary complexes. At higher stoichiometries, Cip1 and Kip1 are potent inhibitors of activated Cdk2, Cdk3, Cdk4. and Cdk6 (Zhang et al., 1993: Gu et al., 1993; Harper et at. 1993). It is believed that Cip1 and Kip1 constitute an activation threshold for progression through the G1 phase of the cell cycle. According to this hypothesis. activation of Cdk2, Cdk4. and Cdk6 cannot occur until the abundance of the corresponding cyclin/Cdk complexes exceeds the concentration required to saturate the "free" pools of Cip1 plus Kip1 (reviewed in Elledge and Harper, 1994; Hunter and Pines, 1994; Sherr and Roberts, 1995; Morgan, 1995).

The mechanism where by Cdks regulate cell cycle progression is complex and by no means complete. However, large amounts of data have been collected regarding how Cdks regulate transition from G1 into S phase. The majority of this work centers around the product of the retinoblastoma tumor suppressor gene, Rb. Rb functions in part by serving as a control point that connects extracellular signals and gene transcription. Rb is a phosphoprotein that is differentially phosphorylated throughout the cell cycle. During G0 or early G1, Rb is present in a hypophosphorylated form and exert its growth suppressive activity (reviewed in Weinberg, 1995; Nevins, 1992; Hinds and Weinberg, 1994). When Rb is present in this form it binds to and inactivates certain members of the E2F transcription factor family. The binding of Rb with E2F blocks E2F-mediated transcription of cellular genes that are required for entry into S phase, such as DNA polymerase ax, and dihydrofolate reductase (reviewed in Nevins, 1992; Farnham et al., 1993; Hinds and Weinberg 1994). G1 cyclin/Cdk complexes are believed to relieve this Rb-mediated suppression by phosphorylating Rb, which results in the release of E2F (Nevins, 1992; Weinberg, 1995). Upon its release E2F can then activate transcription of cellular genes essential for entry into S phase. A schematic of Cdk-mediated inactivation of Rb is shown in FIG. 2.

There is a substantial amount of data indicating that all G1 cyclin/Cdk complexes play critical roles in the initiation of and/or progression through S phase (reviewed in Draetta 1994; Elledge and Harper, 1995; Sherr, 1994), but until substrates besides Rb are found, the specific role for each cyclin/Cdk complex in regulating cell cycle progression will likely remain largely unknown. Anologous results are likely for other DNA viruses dependent on cell cycle stimulatory kinases for replication at least most other species-specfic CMV's.

In vitro mammalian cell systems provide the most studied and best models for DNA virus infections. This is most spectacularly true for HCMV, where there is no accepted animal model. The well-studied in vitro HCMV systems provide a superior model for all mammalian DNA virus infections.

SUMMARY OF THE INVENTION

An important aspect of the present invention is a method for inhibiting proliferation of a DNA virus which is dependent upon events associated with cell proliferation for replication. The DNA virus include, for example any of the herpesvirus family such as Herpes simplex, e.g., and most particularly cytomegalovirus (especially human cytomegalovirus). The method involves administering a prophylactically or therapeutically effective amount of a cyclin-dependent kinase (e.g., Cdk2) inhibitor to a patient. The therapeutically effective amount of inhibitor is that amount sufficient to inhibit Cdk and therefore prevent viral replication. The most preferred inhibitor is roscovitine although olomoucine or other Cdk inhibitors are also acceptable. Once the knowledge of the present invention is available, many other Cdk inhibitors may be developed and these Cdk activity inhibitors will be useful for the therapy and prophylaxis of DNA viral infections. Herpesviruses such as herpes simplex, for example, are also treatable by the methods of the present invention. The preferred therapeutically or prophylactically effective amounts of the Cdk inhibitors of the present invention (e.g., roscovitine, olomoucine and the like) are about 0.1 $\mu$g/kg body weight to about 1000 $\mu$g/kg of body weight (more preferably 0.1 $\mu$g/kg to 100 $\mu$g/kg. However, more effective Cdk or Cdk2 inhibitors would have to be added at lesser concentrations. Likewise, weaker Cdk inhibitors would require greater amounts (i.e., 10–1000 $\mu$g/kg). Other Cdk inhibitors may be readily developed and tested based upon the structures and assay methods described herein or well known to those of skill in the art.

Human cytomegalovirus is a herpesvirus that induces numerous cellular processes upon infection. Among these are activation of cyclin-dependent kinase 2 (Cdk2), which regulates cell cycle progression in G1 and S phase. Inhibition of cellular Cdk2 activity blocks HCMV replication. Inhibition of Cdk2 activity by roscovitine inhibits HCMV DNA synthesis, production of infectious progeny, and late antigen expression in infected cells in a dose-dependent manner. HCMV replication is also inhibited by the expression of a Cdk2 dominant negative mutant, whereas expression of wild type Cdk2 has no effect on viral replication. Activation of cellular Cdk2 is now found necessary for HCMV replication.

HCMV replication is particularly dependent on the activity of cyclin E-Cdk2. Drugs that inhibit the activity of Cdk2 profoundly inhibit virus replication. Drugs that block certain components in the proliferative activation of cells and their progression through the cell cycle also block HCMV replication. Other viruses, particularly DNA viruses and more particularly herpesviruses that are dependent on events activating cell proliferation for replication will be similarly inhibited.

As demonstrated herein. the administration of cytotoxically effective amounts of cdk2 inhibitors may also be used to selectively kill cells infected with a DNA virus such as HCMV, for example.

Administration of the Cdk inhibitors may be parenteral (intravascular, e.g.) enteral or topical (e.g., intracavitary). The topical intracavitary administration may be to any body cavity likely to be a scene for viral infection or to already possess infected cells.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3B illustrates quantitative data representing the mean of two independent experiments in which the abundance of a protein or a complex or the activity of a kinase is expressed relative to the abundance or activity that prevailed at the time of serum addition (O hr).

FIGS. 4A–4B. Cell cycle analysis following productive HCMV infection. LU cells were synchronized by serum deprivation, as described in the Materials and Methods, and infected with HCMV for 1 hr. Thereafter, the viral inoculum was replaced with spent, serum-free media, with (FIG. 4B) or without phosphoroacetic acid (PAA), an inhibitor of viral DNA replication (FIG. 4A). The cells were harvested and stained with propidium iodine at intervals after infection, and the DNA content was determined by flow cytometric analysis.

FIG. 8D schematically shows the structure of roscovitine.

FIG. 9C schematically shows the structure of olomoucine.

FIGS. 11A–11B. Effects of roscovitine on non-infected LU cells. LU cells were treated with 15 $\mu$M roscovitine for 96 hr. After 96 hr cells were stained with propidium iodine and analyzed by flow cytometry (FIG. 11A). In parallel, roscovitine containing medium was removed and replaced with fresh EMEM containing 10% FBS or EMEM containing 10% FBS and bromodeoxyuridine. Cells %%ere harvested 24 hr after removal of roscovitine and analyzed for cell cycle progression by flow cytometry (FIG. 11A) and bromodeoxyuridine incorporation (FIG. 11B).

(FIGS. 13A and 13B) HA antigen (Cdk2) was detected by fluorescein fluorescence to demonstrate cells expressing either wild type or dominant negative Cdk2. (FIGS. 13C and 13D) HCMV UL80.5 late antigens were detected by rhodamine fluorescence. The identical field of cells is shown in FIGS. 13A and 13C. An identical field of cells is also illustrated in FIGS. 13B and 13D.

DESCRIPTION OF ILLUSTRATIVE EMBODIMENTS

Figure 1:
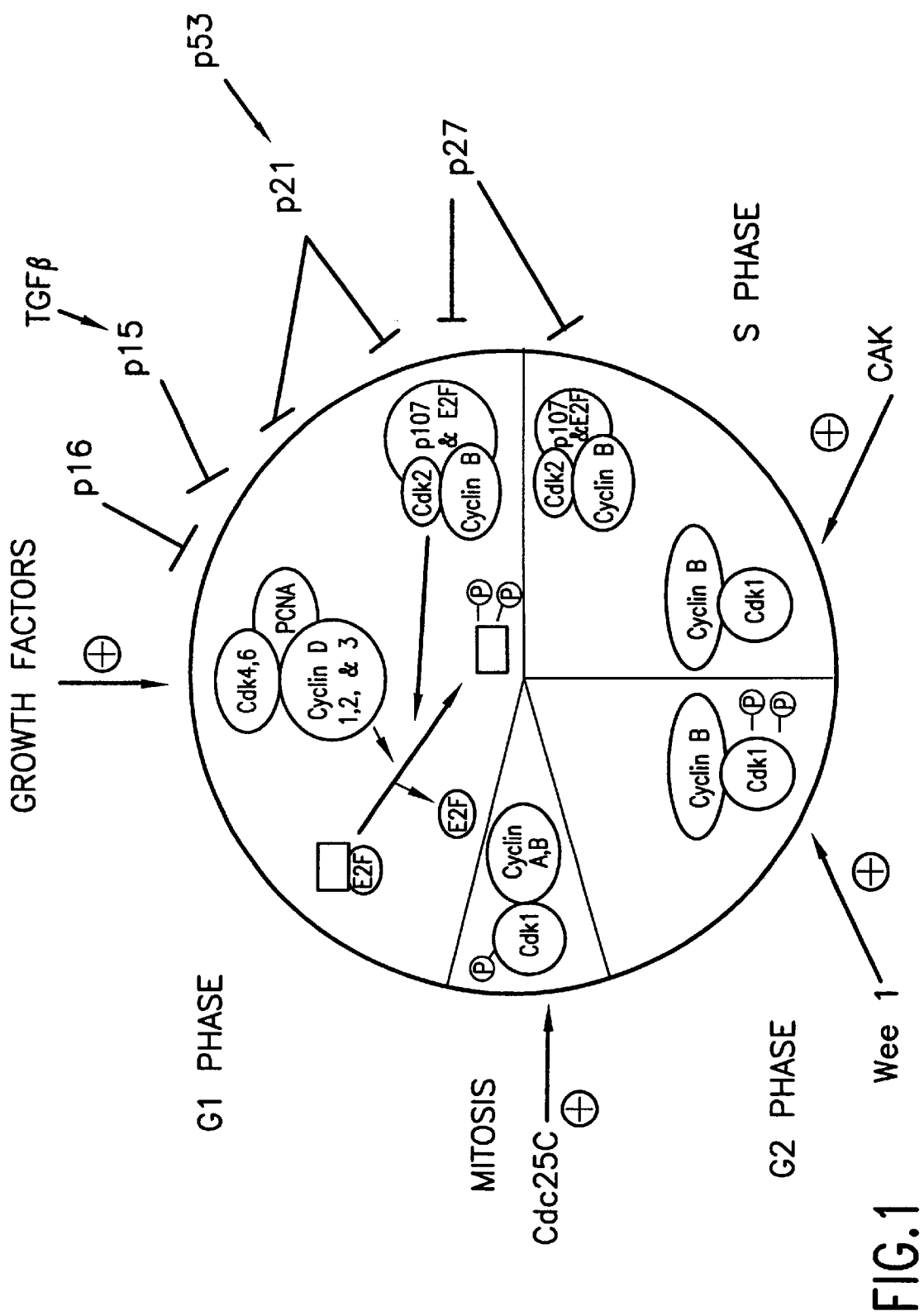
FIG. 1. Cyclin, Cdk, CKI regulation of the cell cycle. Shown is a schematic view representing the points of action for mamnnalian cyclin/Cdk complexes during the cell cycle.

There is an urgent need for the development and application of new drugs against DNA viruses, particularly herpesviruses such as cytomegalovirus, particularly human cytomegalovirus (HCMV) and Herpes simplex. These latter viruses are a major problem in modern medicine, especially when the immune system is compromised. When the immune system is compromised, herpesvirus infections become an important cause of morbidity and mortality. Although a number of drugs have recently become available to treat herpesvirus infections, none of these are entirely satisfactory. Most have a level of toxicity that is problematic, particularly with the long-term treatment often required for herpesviruses. Unfortunately, herpesviruses also develop resistance to these drugs surprisingly quickly. Thus, there is not only a need for new drugs, but more importantly a need for new drugs that act through novel mechanisms. This latter point is important because drugs that function through different mechanisms, when combined, often produce a synergistic effect which may or may not be desirable or might even prove deleterious to the patent. Furthermore, resistance to antivirals occurs much less frequently with drugs working through different antiviral mechanisms. At present, antivirals based on inhibition of Cdk or Cdk2 in particular are not available on the market. Drugs which inhibit Cdk's such as Cdk2 offer the potential for potent antiviral activity through a novel mechanism. Several inhibitor drugs are described and used herein. Others may be developed by using the kinase assays described.

Cell proliferation is know to involve a number of molecular events that are organized into cell cycle stages (C1, S, G2, M). Traverse of the cell cycle is regulated by the activity of a number of kinases (cyclin-dependent kinases or Cdks). The activity of these kinases is in turn controlled by proteins known as cyclins, whose abundance is directly related to the stage of the cell cycle. For example, during G1 the abundance of cyclin E is increased and its catalytic partner, Cdk2, is relocated from the cytoplasm to the nucleus, forming a complex (cyclin E/Cdk2) that phosphorylates regulatory molecules. Phosphorylation of these molecules results in increased transcription of cellular genes encoding proteins that cause the synthesis of molecules required for cellular DNA synthesis. Cyclin E/Cdk2 activity, for example, is associated with substantial increases in the nucleotide precursor pool required for cellular DNA synthesis.

Most of the cells in adult animals, including humans, are terminally differentiated and have a number of impediments to prevent DNA synthesis. For DNA viruses to replicate their DNA in these differentiated cells, they must overcome these constraints. Some DNA viruses such as papovaviruses induce the cell to enter and traverse the entire cell cycle. The DNA genome of these viruses is replicated in part by cellular enzymes along with cellular DNA. For other viruses such as some human herpesviruses. replication in differentiated cells is accomplished in a somewhat different manner. These viruses encode their own enzymes for DNA replication, but still require cellular enzymes to increase the pool of nucleotide precursors required partial traverse of the cell cycle, is human cytomegalovirus (HCMV). HCMV activates density-arrested cells to enter the cell cycle and proceed through G1 to a stage at or near the G1/S boundary. This results in substantial increases in the pool of precursors required for DNA synthesis. The abundance of cyclins required for other cell cycle events, as D and A. is not increased, so the cells are unable to replicate their own DNA and complete traverse of the cell cycle. Accordingly, replication of these viruses is dependent upon limited activation of the cell cycle and, particularly, on activation of cyclin E/Cdk2.

Human cytomegalovirus has long had a suspicious association with accelerated atherosclerosis in heart transplant recipients. More recent studies have also indicated a possible association between HMCV infection and atheroschlierosis in the elderly. HCMV appears likely to pose dangers for the immunosuppressed, such as organ recipients and AIDS patients. Additionally, it is thought that HCMV may play a significant role in the restenosis of cardiac arteries after angioplasty. Thus, the inhibitors and methods of the present invention may serve to prevent or slow atheroschlerosis, untoward side effects of immunosuppression or restenosis, insofar as they are enhanced or caused by HCMV.

Figure 2:
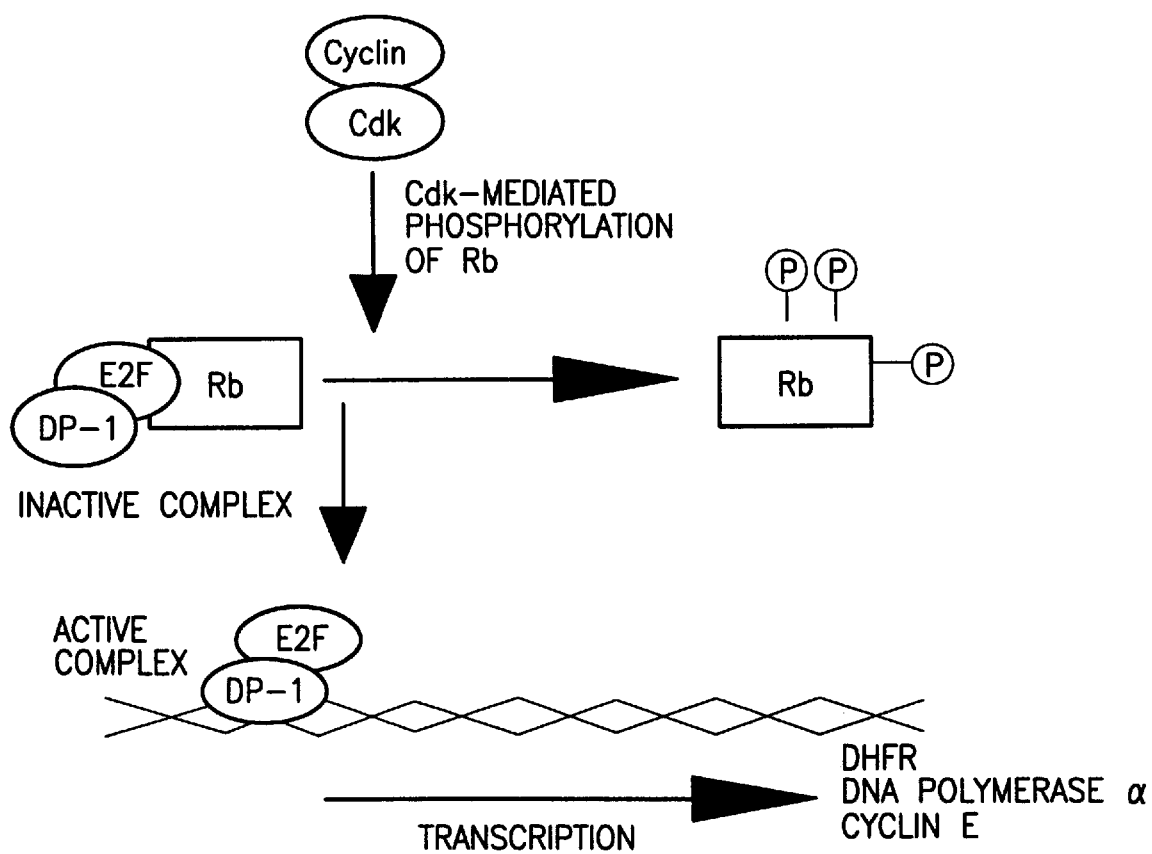
FIG. 2. Cdk-mediated activation of E2F. Schematic diagram demonstrating Cdk-mediated release of E2F from the retinoblastoma protein.
Figure 2A:
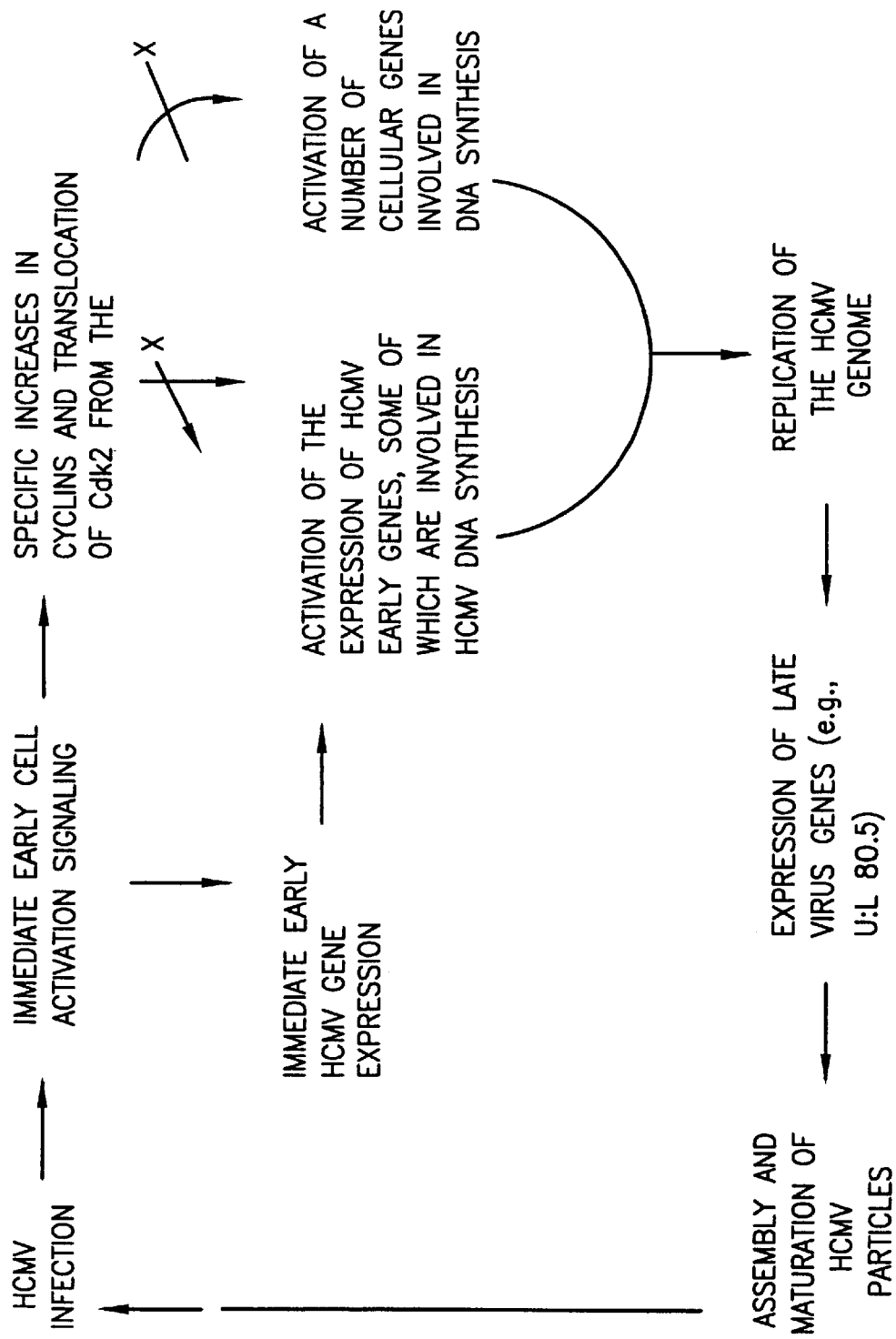
FIG. 2A. Schematically shows some key events in HCMV replication and points of inhibition by the methods of the present invention.

The application of anti-Cdk2 drugs to virus infections is not a mere improvement over prior technology, but is a novel approach to the treatment of virus infections. A scheme illustrating some of the key events in the replication of HCMV is shown in FIG. 2A. Also illustrated in FIG. 2A are the most probable sites of action of these compounds based on the current understanding of the replication of HCMV. The present invention provides in vitro studies with human cells which will allow those of skill in the art to develop a human treatment regimen without undue experimentation.

One objective of these studies was to determine genes and/or their products that were required for HCMV replication. The inventors were particularly interested in investigating the role that G1 cyclins and Cdks play in HCMV infection. Early results indicated that HCMV infection of permissive cells resulted in an increase in cyclin E abundance and kinase activity. Before investigating this observation further, the inventors obtained a better understanding of how cyclin E/Cdk2 activity was controlled during progression from G0 to S phase in serumstimulated cells, to compare these findings with those obtained for HCMV-infected cells. The current model for cyclin E/Cdk2 activation holds that cyclin E/Cdk2 complexes are not active until they have overcome a threshold set by two cyclin kinase inhibitors Cip1 and Kip1 (Elledge and Harper, 1994; Hunter and Pines, 1994). This model provides for numerous ways to overcome the threshold set by Cip1 and Kip1. The simplest model involves increasing the abundance of cyclin E and thereby increasing the formation of cyclin E/Cdk2 complexes. Another possible way is by inhibiting the expression of either Cip1 or Kip1. However, data obtained by Ohtsubo (1995) indicate that the activity of cyclin E/Cdk2 in G0 cells is not directly or in any simple way related to the abundance of cyclin E or Cdk2 or to the binding of CKIs to cyclin E/Cdk2 complexes. Such data suggest a level of complexity that is not presently understood, or the existence of regulatory mechanisms that have not been appreciated to date.

The examples described herein are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. For example, although HCMV is the primary DNA virus studied, this is also the best characterized system for DNA viral study. It is also noted that there is no accepted animal model for HCMV infection, the virus being species-specific. It is believed that other specific CMV's will react similarly.

MATERIALS AND METHODS

Cell Culture

Human diploid embryonic lung fibroblasts (LU) (Albrecht et al., 1980a), passage 12–20, or U-373 MG astrocytoma cells were cultured in Eagle's Minimum Essential Medium with Earle's salts (EMEM) with 10% fetal bovine serum (FBS) and penicillin (100 units/ml)/streptomycin (100 $\mu$/ml) at 37° C. in a 5% $CO_2$ atmosphere. To obtain serum-arrested cultures, LU cells were grown to 70–80% confluence. The medium was then removed and the cells were washed with warm, serum-free EMEM. After washing, fresh, serum-free EMEM was placed on the cells and the incubation continued for another 48 hr to achieve growth factor arrest. After serum-deprivation, the serum-free medium was decanted and reserved. The cells were either infected with HCMV, mock-infected, or stimulated with 20% FBS in fresh EMEM. To obtain density-arrested cultures, the cells were initially grown to confluence. The medium was replaced with fresh EMEM containing 10% FBS, and the cells were incubated another 48 hr to insure strict density arrest. The cells were then either infected with HCMV, mock-infected, or stimulated with 10% FBS in fresh EMEM. Subconfluent or confluent cells were harvested at intervals after HCMV infection, mock infection, or serum stimulation and processes for various assays as described below.

Virus Propagation

Human cytomegalovirus strain AD169 (passage 86–92) was used. Virus stocks were prepared by infecting confluent monolayers of LU cells at a multiplicity of infection (M.O.I.) of 5 plaque forming units (PFU)/cell. Infected cultures were maintained in EMEM containing 10% fetal bovine serum (FBS), and frozen 4–5 days post-infection. Viral stocks were prepared by releasing the virus from the cell by freeze-thaw and sonication (2×30 sec). Virus was aliquoted and stored at −80° C. Before use the cellular debris was removed by sedimentation.

Virus Infectivity Assay

Virus infectivity was determined as described previously by Albrecht and Weller (1980). Briefly, confluent LU cell monolayers in 35 mm dishes were infected with 10-fold serial dilutions of virus stock at 37° C. for 1 hr. The virus inoculum was removed and replaced with 1.5 ml of agarose overlay containing EMEM, 10% FBS, 0.25% agarose, and 0.225% sodium bicarbonate. After 7 days incubation an additional 1.5 ml of overlay was added and the dishes incubated 7 more days. After 14 days total incubation, cells were fixed with 10% formalin and stained with 0.03% methylene blue and plaques counted with the aid of a dissecting microscope.

Virus Infection

Virus stock was added to a calculated multiplicity of infection of 5 PFU/cell. The virus inoculum or mock-infecting fluids were removed after 1 hr. For infection of subconfluent cultures, the cells were maintained after removal of the virus in the reserved "spent" serum-free medium. For confluent cells, the virus inoculum and mock-infecting fluids were removed and replaced with warm EMEM containing 2% FBS. For mock infection, cells were exposed to mock-infecting fluids (Boldogh et al., 1990) containing no virus particles for 1 hr.

Roscovitine Treatment of Infected Cells

Confluent monolayers of LU cells were infected at a M.O.I. of 5 PFU/cell and allowed to absorb for 1 hr at 37° C. The virus inoculum was removed and replaced with warm EMEM containing 2% FBS and the indicated concentration of drug or vehicle. Cells were harvested 96 hr post-infection and assayed for infectivity as described above, or cells were harvested 72 hr post-infection and HCMV DNA abundance determined by slot blot hybridization.

Virus Purification

Virus particles were pelleted by sedimentation from clarified virus stocks by certification at 100.000×g in a SW28 rotor (Beckman) for 90 minutes at room temperature. Following certification the supernatant was decanted and reserved (virus-free supernatant). The pelleted virus was resuspended in serum free EMEM and subsequently used for infection.

UV Irradiation of Virus

To inhibit HCMV gene expression, virus stocks were UV-irradiated on an ice bed at 254 nm at a dose rate of $8\times10^{-6}$ $J/s/mm^2$, for 30 minutes as described previously (Boldogh et al., 1990). Under these conditions HCMV gene expression is abolished (Boldogh et al., 1990). To ensure that UV-irradiation protocol inhibited HCMV gene expression, cells were infected with HCMV or UV-irradiated HCMV and stained for the expression of HCMV immediate early (IE) proteins.

Flow Cytometry

Cells were harvested by trypsinization at selected times after virus infection, mock infection, or serum stimulation. The cells were washed in PBS, collected by sedimentation, suspended in low salt buffer [3% polyethylene glycol, propidium iodine (5 $\mu$g/ml), 0.1% Triton-X, 4 mM sodium citrate, RNase A (100 $\mu$g/ml, added just before use)], and incubated 20 min at 37° C. High salt buffer [3% polyethylene glycol, propidium iodine (5 $\mu$g/ml), 0.1 % Triton X-100, 400 mM NaCl] was added, and the cells were maintained at 4° C. overnight. The cellular DNA content was analyzed using a Becton-Dickinson FACS can flow cytometer.

Isotopic Labeling, Isolation and Analysis of DNA

Subconfluent, serum-arrested cells were pulse-labeled for 6 hr with 10 mCi/ml [$^3$H]methyl thymidine (52.74 Ci/mmole). At the end of the pulse, the cultures were rapidly frozen and thawed for 2 cycles to dislodge the cells. DNA was released and analyzed by isopycnic centrifugation as described previously (Albrecht et al., 1980b).

Western Blotting

Cells were harvested by trypsinization, collected by sedimentation, and lysed in NP-40 lysis buffer (50 mM Tris, pH 7.4, 150 mM NaCl, and 0.5% NP-40, with 1 mM NaVO3, 50 mM NaF, 1 mM PMSF, 1 mM DTT, 25 μg/ml leupeptin, 25 μg/ml trypsin inhibitor, 25 μg/ml aprotinin, 1 mM benzamide, and 25 μg/ml pepstatin A added just before use). Cellular debris was removed by sedimentation and the supernatant fluids reserved. The protein concentration was determined by the method of Bradford (Bradford, 1976). Equal amounts (40 μg) of protein were resolved by electrophoresis in the presence of SDS on 10–12.5% polyacrylamide gels (SDS-PAGE). Proteins were transferred to nitrocellulose membrane (Bio-Rad) and probed with specified antibodies. Immunoreactive proteins were detected by the ECL chemiluminescent system (Amersham), and specific bands were quantified by densitometry (Applied Imaging Lynx 5000).

Indirect Immunofluorescent

Cells were cultured on sterile glass coverslips. The cells were washed three times in PBS and fixed in acetone:methanol (1:1) at −20° C. for 10 min. The permeabilized cells were incubated with primary antibody diluted in PBS for 1 hr at 37° C. in a humidified chamber. After 2 washes in PBS for 15 min, the cells were incubated with a secondary antibody (affinity-purified, goat anti-mouse or rabbit FITC-conjugated IgG) for 45 min. The excess conjugate was removed by washing the cells in PBS for 30 min. After drying, the cells were mounted in PBS/glycerol (1:1) and examined with the aid of a Zeiss Photomicroscope III using a 40/1.0 Neofluar lens. Images were photographed on Kodak Ektachrome Elite 400 color slide film.

Histone H1 Kinase Assay

Kinase assays were accomplished as described previously (Dulic et al., 1992). Briefly. aliquots containing 150 μg of protein were incubated with antibody for 2 hr at 4° C. The protein/antibodies complexes were then precipitated using Protein A-Sepharose beads. The pellets were washed 3 times with NP-40 lysis buffer, followed by washing 3 times with 2×kinase buffer (40 mM Tris-HCl, pH 7.5, 8 mM $MgCl^2$). Kinase reactions were undertaken in tubes containing the precipitates in a total volume of 5 μl, which included 3 μl 2×kinase buffer containing 2.5 μg histone H1(GIBCO BRL) and 2 μl (4 μCi), [γ-32P] ATP (10 Ci/mmol, DuPont NEN) at 37° C. for 30 min. The reaction was stopped by the adding 5 μl 2×sample buffer and boiling for 5 min. Each sample was then separated by SDS-PAGE following standard protocols well-known to the skilled artisan. The gels were dried and exposed to Kodak XAR-5 film. Specific bands were quantified by densitometry.

Transient Transfections

U-373 cells were split 1:3 24 hr prior to transfection into 100 mm dishes. Cells were transfected with either 10 μg of pCMVCdk2-wt-HA or pCMVCdk2-dn-HA with Tfx-50 lipofection reagent (Promega) at a 3:1 lipofectin:DNA ratio for 2 hr. Cells were either removed with trypsin and seeded into 35 mm dishes containing sterile glass coverslips, and cultured 24 hr before being infected as described above. or cells were harvested 48 hr after transfection and processed for western blotting and kinase assays.

Slot Blot Hybridization

Total DNA from cells was isolated by phenol extraction as described by Boldogh et al. 1990. Equal aliquots of DNA (2 μg) were heated to 95° C. and transferred to lybond+ (Amersham) membranes in 10×SSC (1×SSC: 0.15M NaCl, 0.015M sodium citrate) buffer using a slot blot apparatus. Membranes were denatured for 5 min in 0.5M NaOH—1.5M NaCl buffer and neutralized in 1.5M NaCl, 0.5M Tris-HCl pH. 7.2, 0.001 M EDTA buffer for 5 min, and then dried for 10 min in a vacuum oven at 80° C. Filters were prehybridized in Rapid-Hyb buffer (Amersham) for 3 hr at 60° C. Hybridization was carried out by overnight incubation in the same buffer at 60° C. A 253 bp PCR™ amplified immediate early fragment from HCMV strain AD169 was $^{32}P$ labeled by random priming (Promega) as described by the manufacturer and used as probe. Filters were washed twice in 0.1% SDS in 2×SSC at room temperature for 15 minutes, then 0.1% SDS in 0.2×SSC at 60° C. for 20 min and exposed to film (Kodak XAR-5) at −80° C.

Isolation of Nuclei

Cells were washed with PBS and removed from the flask by scraping. Cells were sedimented by centrifugation and resuspended in 1 ml of PBS and transferred to a 1.5 ml centrifuge tube. The cells were again centrifuged and the supernatant removed by suction. The pellet was resuspended in lysis buffer (0.25 M NaCl, 50 mM Tris-HCl; pH 7.4, 50 mM EDTA) by pipetting and vortexing so no cell aggregates were present. NP40 was added to a final concentration of 0.5% and the suspension mixed by inversion for 3–5 minutes. Nuclei were sedimented by centrifugation and the cytoplasm (supernatant) fraction reserved. The nuclei pellet was resuspended in 1 ml PBS and again sedimented and the supernatant removed by suction. The pellet was resuspended in lysis buffer and SDS was added to a final concentration of 0.5% and mixed by inversion for 5 minutes. The nuclear lysates were then clarified by centrifugation (60,000×g at 2° C. for 20 minutes). The supernatant removed and saved for western blotting.

Image Processing

Chemilumeniescent samples were exposed for intervals that assured linearity of response. as determined by standardization. All radiographic films were analyzed using the Applied Imaging Lynx 5000 digital work station with Lynx V5.5 software. The images were quantified and recorded as tagged image format files (TIFF). The TIFF were used to prepare the graphic images.

Hematoxylin-Eosin Staining

Cells were prepared on glass coverslips inserted into flat bottom 35 mm dishes. At appropriate times following the initiation of virus infection and incubation, infected and control coverslip cultures were removed, rinsed three times in PBS and placed in Bouin's picric acid fixative. The cells remained in the fixative from 1 hr to overnight, at which time the coverslips were transferred to 70% ethanol for a minimum of 24 hr. The fixed cells then were rehydrated in decreasing concentrations of ethanol (5 min. each) and placed in Harris' hematoxylin (15 min.). The hematoxylin-stained coverslips were destained briefly in 0.4% hydrochloric acid, rinsed in distilled water, and placed in Scott's blueing solution (0.1% lithium carbonate) for 5 min. Following dehydration in increasing concentrations of ethanol (5 min. each), the coverslips were placed in alcoholic eosin solution (10 min.). After complete dehydration in absolute ethanol (total 20 min.) and xylene (total of 20 min.), the coverslips were mounted in cytoseal mounting medium and allow to dry.

Formation of Cyclin E/Cdk2 Complexes, Induction of Cyclin E, and Activation of Cyclin E-Dependent Kinase.

Figure 3A:
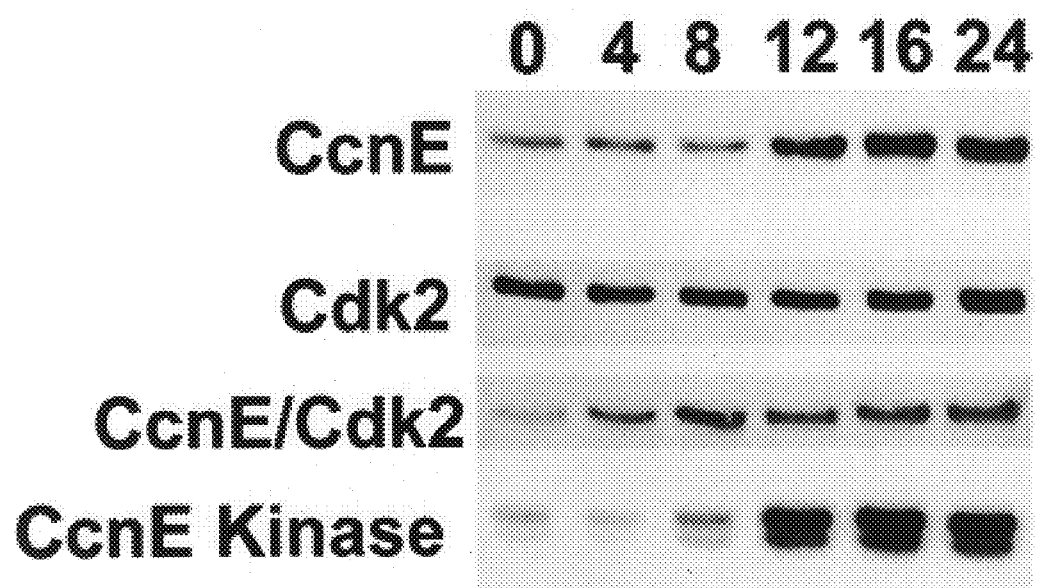
FIGS. 3A–3B. Cyclin E, Cdk2, and cyclin E/Cdk2 complexes after serum stimulation of GO-arrested cells. Fibroblasts at 70–80% confluence were synchronized in a quiescent state (GO) by sennm starvation for 48 hr and then stimulated by adding fresh EMEM with 20% FBS. (See Table 1) Cells were harvested at intervals, stained with propidium iodine, and the DNA content was determined by flow cytometry. Cell lysates were also prepared at intervals after stimulation, and resolved by SDS-PAGE. The resolved proteins were transferred to nitrocellulose and probed with either cyclin E (CcnE), or Cdk2 antibodies (FIG. 3A). The cell lysates were also immunoprecipitated with cyclin E antibody. The precipitates were resolved by SDS-PAGE, followed by immunoblotting with an antibody against Cdk2 (CcnE/Cdk2 in FIG. 3A). In addition, immunoprecipitated formed with cyclin E antibodies were assayed for the ability to phosphorylate histone H1 (FIG. 3A) as described in the Materials and Methods.

The studies described below were carried out in serum-arrested human diploid fibrobroblasts stimulated with serum to enter into the cell cycle. These cells exhibited synchronous progression through G1 following serum stimulation as illustrated by the data shown in FIG. 3A. The majority of these cells maintain a G1 DNA content for 16 hr after addition of serum. Bromodeoxyuridine (BrDU) labeling of such cultures indicated that <5% of the cells had accumulated detectable amounts of BRdU-labeled DNA within 16 hr after stimulation. The cells rapidly entered S phase between 16 and 24 hr after addition of serum. As shown in FIG. 3A, at least 70% of the cells exhibited >2N DNA content at 24 hr, and BRdU labeling studies indicated that >85% of the cells in these cultures initiated DNA replication between 16 and 24 hr.

Cyclin E protein was induced after serum stimulation of quiescent human diploid fibroblasts. as shown in FIG. 3A. FIG. 3A contains data from a representative study, and FIG. 3B contains quantitative data representing the average of two such studies. The abundance of cyclin E (CcnE, open circles, FIG. 3B) increased slowly during the first 8 hr after serum stimulation. Thereafter. the amount of cyclin E increased rapidly from 8–12 hr to 16 hr, increasing about five fold and remaining relatively constant for the duration of the study. Cdk2 expression was more or less constant, increasing slightly between 16 hr and 24 hr after stimulation (triangles, FIG. 3B). Although both cyclin E and Cdk2 remained relatively constant during early G1 (the first 8 hr after serum stimulation), the abundance of the cyclin E/Cdk2 complex increased significantly within 4 hr after addition of serum (CcnE/Cdk2, filled circles, FIG. 3B). Despite the rapid increase in cyclin E/Cdk2 complexes during early G1 progression, there was little or no increase in cyclin E-dependent histone H1 kinase activity (E Kinase, filled squares, FIG. 3B) during the first 8 hr after serum stimulation. Table 1 summarizes some of these results.

TABLE 1

CELL CYCLE DISTRIBUTION OF SERUM-STIMULATED 18LU CELLS

| Hours | % Cells in G1/G0 | % Cells in S | % Cells in G2/M |
|---|---|---|---|
| 0 | 93.8 (1.3) | 1.6 (0.2) | 5.1 (1.0) |
| 4 | 91.8 (0.2) | 2.5 (0.4) | 5.7 (0.6) |
| 8 | 91.3 (0.7) | 1.9 (0.2) | 6.8 (0.9) |
| 12 | 87.5 (1.4) | 4.5 (1.7) | 7.9 (0.4) |
| 16 | 89.4 (0.8) | 3.8 (0.8) | 6.0 (1.2) |
| 24 | 29.2 (1.4) | 32.6 (0.5) | 38.2 (1.8) |

Subcellular Localization of Cdk2, Cyclin E, Cip1, and Kip1

Association between cyclin E and Cdk2 in quiescent cells could be inhibited by sequestration of either protein. This inhibition could be affected by an inhibitor that prevents formation of the binary complex, although no such inhibitor is known for Cdk2. Alternatively, sequestration could be affected by compartmentalization of cyclin E and Cdk2. Immunocytochemical studies were carried out to determine if cyclin E and Cdk2 share the same intracellular location in G0 cells.

Figure 3B:
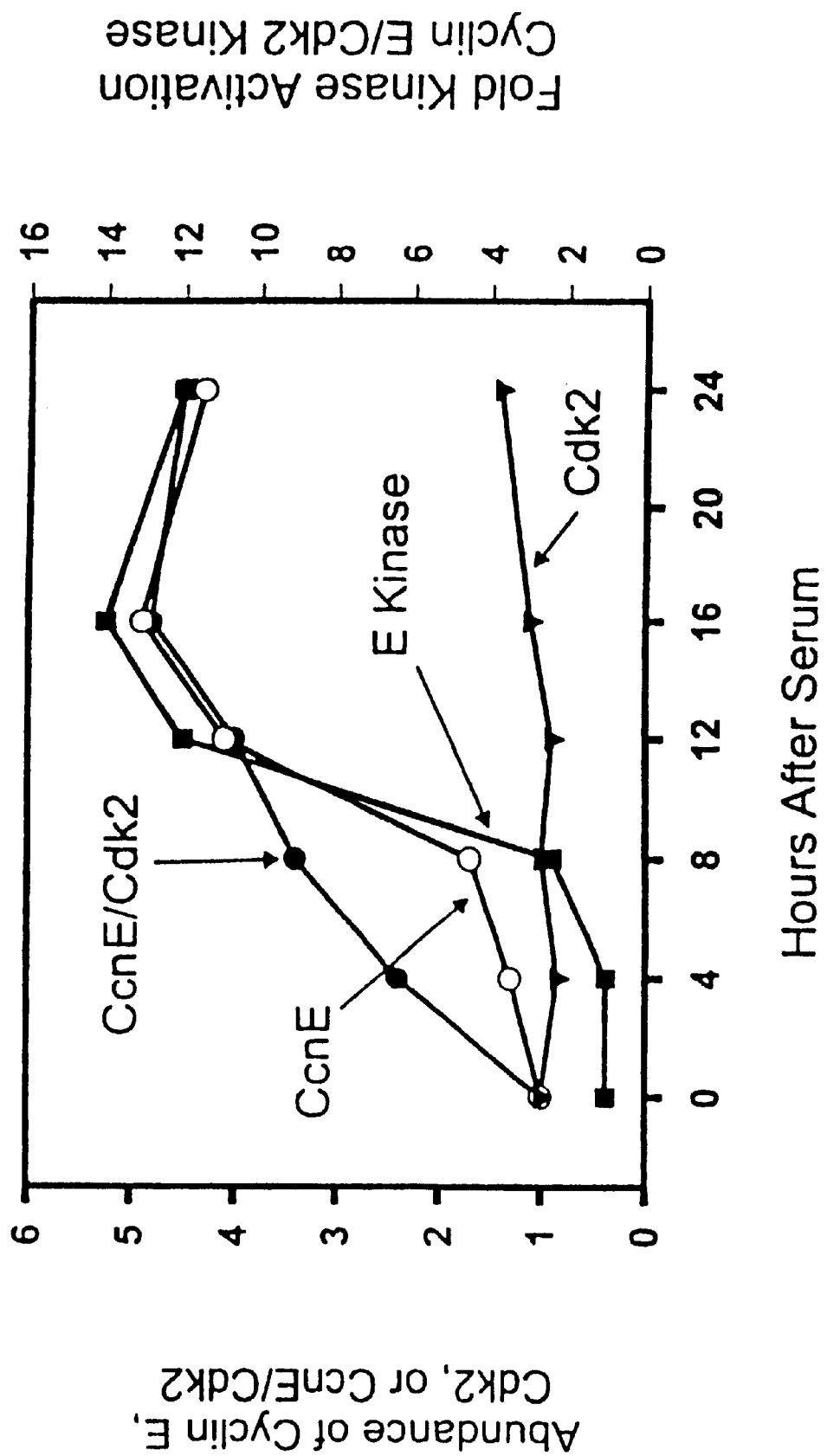

Activation of E/Cdk2 Kinase During Early G1 Progression is Constrained by a CKI Threshold The data shown in FIG. 3B indicate that neither induction of cyclin E, nuclear uptake of Cdk2, nor formation of cyclin E/Cdk2 complexes is sufficient to account for the kinetics of activation of cyclin E/Cdk2 kinase; although all three of these parameters are clearly important to kinase activation. For example, cyclin E-associated histone kinase activity (squares, FIG. 3B) did not being to increase until about 8 hr after serum stimulation, although cyclin E/Cdk2 complexes (fillesd circles, FIG. 3B) had achieved near maximum levels within this period of time. The day in activation of cyclin E-dependent kinase, relative to formation of cyclin E/Cdk2 complexes, suggests that kinase activity in early G1 may be constrained by a cyclin kinase inhibitor thereshold.

Cellular And Viral DNA Synthesis During Productive HCMV Infection.

The DNA content of serum-arrested, HCMV-infected, subconfluent LU cells was analyzed by flow cytometry to determine to what extent productively infected cells initiate DNA synthesis. The results of a representative study are shown in FIG. 4A, and quantitative data are given in Table 2. Infected cells maintained a 2N DNA content for 24 hr after infection. Total DNA content of infected cells began to increase within 48 hr, and a substantial number of cells with >2N DNA content was observed 72 hr after infection. No increase in DNA content was observed in mock-infected cells. When confluent cultures were infected with HCMV, the results were essentially identical to those shown in FIG. 4A.

TABLE 2

Cell Cycle Distribution Following HCMV Infection

| Treatment | Percent Cells in phase[a] | Hours After Treatment | | | |
|---|---|---|---|---|---|
| | | 0 | 24 | 48 | 72 |
| HCMV[b] | G0/G1 | 93.3 (1.2) | 91.9 (0.3) | 94.5 (2.2) | 74.8 (3.9) |
| | S | 1.6 (0.2) | 1.6 (0.6) | 3.8 (1.3) | 25.1 (3.9) |
| | G2/M | 5.1 (1.0) | 6.5 (0.3) | 1.8 (1.0) | 0 |
| HCMV[b] + PAA[c] | G0/G1 | 93.3 (1.2) | 97.2 (0.4) | 97.1 (0.8) | 97.2 (0.3) |
| | S | 1.6 (0.2) | 0.9 (0.1) | 1.5 (0.4) | 1.9 (0.3) |
| | G2/M | 5.1 (1.0) | 1.9 (0.3) | 1.3 (0.4) | 0.9 (0.1) |

[a]The percent of cells in G0/G1, S, or G2/M of the cell cycle was determined following HCMV infection of subconfluent LU cells in the absence (HCMV) or presence of phosphonoacetic acid (HCMV + PAA). The data represent the average of three studies with standard deviation shown in parentheses.
[b]5 PFU/cell
[c]100 µg/ml LU cells are productive for HCMV infection (Albrecht et al., 1980a); so the increase in DNA content that one observes after HCMV infection must, at least in part, be due to viral DNA replication. The relative contributions of viral and cellular DNA synthesis in productively infected cells was initially analyzed using phosphonoacetic acid (PAA), which, at a concentration of 100 µg/ml (0.75 mM), blocks viral DNA replication in human lung fibroblasts with little or no effect on cellular DNA synthesis or population doubling times of uninfected cultures (Huang, 1975). Expression of the viral late antigen pp28 requires replication of the HCMV genome (Depto and Stenberg, 1992; Re et al., 1985; Meyer et al., 1988), and pp28 expression could not be detected at any time between 24 and 96 hr after infection of LU cells in the presence of PAA. However, when cells were infected in the absence of PAA, antibodies against pp28 produced intense immunofluorescence beginning 24 hr after addition of the virus. The observation that PAA inhibits pp28 expression is consistent with the conclusion that the inhibitor blocks viral DNA replication. The specificity of PAA was confirmed by measuring cellular DNA content after serum stimulation of quiescent LU cells in the presence and absence of PAA. About 68% of serum-starved LU cells entered S, G2 or M phase within 24 hr after addition of serum in the absence of the inhibitor. When cells were stimulated with serum in the presence of PAA, about 57% of the cells were in S, G2, or M phase within 24 hr. These data indicate that, under the conditions employed in these studies, PAA is a specific inhibitor of viral DNA synthesis.

Having confirmed the specificity of PAA as an inhibitor of viral DNA replication, the inventors proceeded to analyze the DNA content of LU cells as a function of time after HCMV infection of subconfluent cells in the presence of PAA. As shown in FIG. 4B. there was no detectable increase in DNA content, under these circumstances. This observation indicates that the increase in total DNA content that one observes after viral infection depends upon viral DNA synthesis and is consistent with the hypothesis that all or most of the DNA that is synthesized after viral infection is viral DNA.

The inhibitor studies shown in FIGS. 4A and 4B indicate that viral DNA synthesis is necessary for the increased DNA content that is observed in HCMV-infected LU cells. However, this observation does not rule out the possibility that viral late gene products may induce host cell DNA synthesis; PAA may block the accumulation of these hypothetical viral gene products, and indirectly inhibit synthesis of cellular DNA. Metabolic labeling of cellular and viral DNA was used to discriminate between these alternatives.

Activation of Cyclin E/Cdk2 Kinase in HCMV-Infected Cells

Since HCMV elicits early mitogenic signaling but fails to induce cellular DNA synthesis, the effects of HCMV on G1 cyclins and Cdks were examined to measure aspects of cyclin/Cdk activation in HCMV-infected LU cells. The inventors examined the effects of HCMV on subconfluent, growth factor-deprived cells which are capable of undergoing G0→S phase progression after serum stimulation, and on density-arrested cells which are incapable of initiating significant DNA synthesis after serum stimulation. Effects of the virus have been contrasted with those of serum growth factors, which stimulate cell cycle progression by a mechanism that is partially understood (reviewed in Sherr, 1994; Draetta, 1994; Sherr, 1993).

The inventors first looked at the effect HCMV-infection has on cyclin E in subconfluent, serum-arrested LU cells. Cyclin E protein was induced within 12 hr after HCMV-infection (FIG. 11A). The effect of the virus was significantly more robust than that of serum growth factors. Cyclin E protein was induced >10-fold by HCMV and never more than 5-fold by serum. The inventors observed no significant induction of cyclin E in mock-infected cells, demonstrating that the inventors' infection protocol does not result in serum-dependent mitotic stimulation which might complicate interpretation of the results of viral infection.

Serum stimulation of subconfluent, serum-starved LU cells caused a 2-fold increase in Cdk2 abundance; whereas neither the virus nor mock infection induced the catalytic partner of cyclin E. The activity of cyclin E/Cdk2 kinase increased over 100-fold after HCMV infection, as evidenced by the ability of cyclin E immunoprecipitates to phosphorylate histone H1. The effect of scrum was less dramatic, although the activity of cyclin E-associated histone H1 kinase increased about 20-fold after serum stimulation of subconfluent cells. Mock infection had no effect on cyclin E/Cdk2 activity.

The inventors noted that the kinetics of induction of cyclin E did not precisely correlate with those of activation of the cyclin E-dependent kinase in HCMV-infected cells. For example, cyclin E protein reached 80% of maximum expression within 12 hr after infection, whereas cyclin E-associated histone H1 kinase activity was only about 10% of maximum at this time (FIG. 12C). This observation suggested that activation of cyclin E kinase might be constrained by a cyclin kinase inhibitor threshold (reviewed in Elledge and Harper, 1994; Hunter and Pines, 1994; Sherr and Roberts, 1995). Accordingly, the inventors measured the effects of HCMV on expression of the two principle Cdk2 inhibitors, Cip1 and Kip1.

The abundance of Cip1 decreased rapidly after infection of subconfluent cells. Serum stimulation increased Cip1 expression, as previously reported by others (Li et al., 1994; Nakanishi et al., 1995). HCMV infection also inhibited expression of Kip1, although the rate of inhibition was less rapid than that observed for Cip1. The kinetics of kinase activation lag behind those of cyclin E induction, suggesting the existence of a cyclin kinase inhibitor threshold. This threshold is overcome about 12 hr after infection, as the expression of Cip1 decreases rapidly. Kip1 expression is reduced no more than 50% in 24 hr; nevertheless, a small decrease in the amount of such an inhibitor may have a significant effect if activation of Cdk2 is precluded until the binding capacity of both Cip1 and Kip1 is exceeded. Likewise, the transitory increase in Cip1 that the inventors routinely observe after addition of the virus may be significant in terms of setting a higher cyclin kinase inhibitor threshold during the first few hours after infection.

HCMV has in common with serum growth factors the ability to activate key G1 progression factors in quiescent, subconfluent cells. However, the normal cellular targets of HCMV are not subconfluent cells. It is known that contact-arrested cells are recalcitrant to serum growth factor stimulation of G1 progression, and the inventors felt that it was important to determine if HCMV was able to activate G1 progression in such cells. Obviously, none of the effects that the inventors have described would have any significance if they cannot be demonstrated in confluent cultures. HCMV induced cyclin E and activated cyclin E-associated histone H1 kinase with little or no effect on Cdk2 expression. Serum had no significant effect on any of these parameters in contact-inhibited cells. Peak induction of cyclin E occurred 24 hr after infection of confluent cultures: whereas maximum activation of cyclin E/Cdk2 kinase was observed at 48 hr. As was the case with subconfluent cells, activation of Cdk2 attended inhibition of cyclin kinase inhibitor expression. Both Cip1 and Kip1 were inhibited in HCMV-infected cells. The kinetics of inhibition were somewhat slower than those observed in subconfluent cells, and closely paralleled activation of cyclin E-associated kinase activity. The data suggest that the kinetics of activation of cyclin E/Cdk2 kinase are strongly influenced by inhibition of Cip1 in HCMV-infected cells. Inhibition of Kip1 expression may contribute to a lesser extent.

HCMV Gene Expression and Cyclin E-dependent Kinase Activation.

Cell cycle progression could be due to a direct effect of HCMV gene products.

Figure 5:
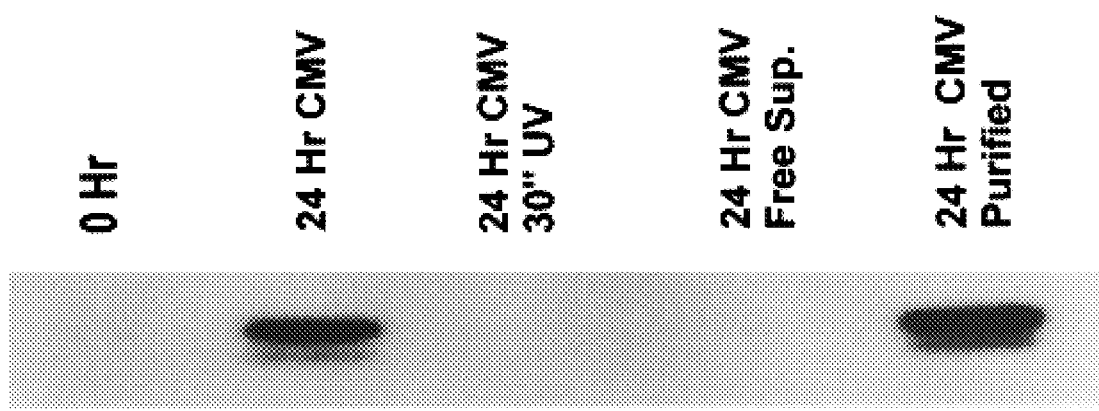
FIG. 5. HCMV gene expression and activation of cyclin E-dependent kinase. Density-arrested LU cells were infected with stock HCMV, HCMV that had been UV-irradiated for 30 min, purified HCMV, or virus-free supernatant prepared from the virus stock. The procedures for virus purification and irradiation are described in the Materials and Methods. After 24 hr, the cells were harvested and assayed for cyclin E-associated kinase activity.

Alternatively, the effects that the inventors have observed could be due to cellular factors elaborated by the cells that were used to propagate the virus and therefore present in the viral inoculum. Studies were undertaken to discriminate among these alternatives. Initially, the inventors determined that UV irradiation of the virus blocked induction of cyclin E and activation of cyclin E/Cdk2 (FIG. 5). Under the conditions employed in this study, the extent of irradiation was sufficient to inactivate detectable HCMV gene expression (Boldogh et al., 1990). No immediate early gene expression was detected when cells were infected cyclin A promoter (Schulze et al., 1995). The observation that HCMV-infected fibroblasts neither initiate DNA synthesis nor induce cyclin A suggested that the virus might fail to induce the D-type cyclins. The inventors measured the abundance of cyclin D1 and its catalytic partner Cdk4 after HCMV infection of confluent cells. Cyclin D1 was not induced by the virus. Rather, the abundance of cyclin D1 decreased at about the time that cellular DNA synthesis stopped and viral DNA synthesis commenced. The expression of Cdk4 did not change during the course of viral infection. Similar results were obtained with subconfluent cultures.

The inventors also examined the phosphorylation state of Rb (product of retinoblastoma gene) following HCMV infection. LU cells were serum-arrested and then either stimulated with serum or infected with HCMV as described in materials and methods. Twenty four hours later the cells were harvested and cell lysates assayed for Rb expression by western blotting. Serum-arrested cells (0 hr) only exhibited the hypophosphorylated form of Rb. Upon serum stimulation Rb became highly phosphorylated exhibiting at least three distinct phosphorylation states. HCMV-infection also resulted in phosphorylation of Rb although the phosphorylation pattern differed from that observed for serum stimulation.

Since cyclin E/Cdk2 activity is induced when G0 cells are infected with HCMV, the inventors examined whether the virus could promote nuclear uptake of Cdk2 in a fashion similar to that observed for serum. To determine whether HCMV is capable of causing Cdk2 translocation into the nucleus of serum-arrested cells, LU cells were grown on glass coverslips and arrested by serum-deprivation when they were 70–80% confluent. After 48 hr serum-deprivation the cells were either fixed for immunofluorescence, stimulated by addition of 20% FBS in EMEM, or infected with HCMV as described previously (Bresnahan et al., 1996a). Infected cells were maintained in the reserved "spent" serum-free media to ensure that no stimulation would result from the presence of serum growth factors. The cells were fixed 24 hr after virus infection or serum stimulation. Cdk2 antigen was detected by immunofluorescence using an anti-Cdk2 antibody and a FITC-conjugated secondary antibody as previously described (Bresnahan et al., 1996b).

Figure 6:
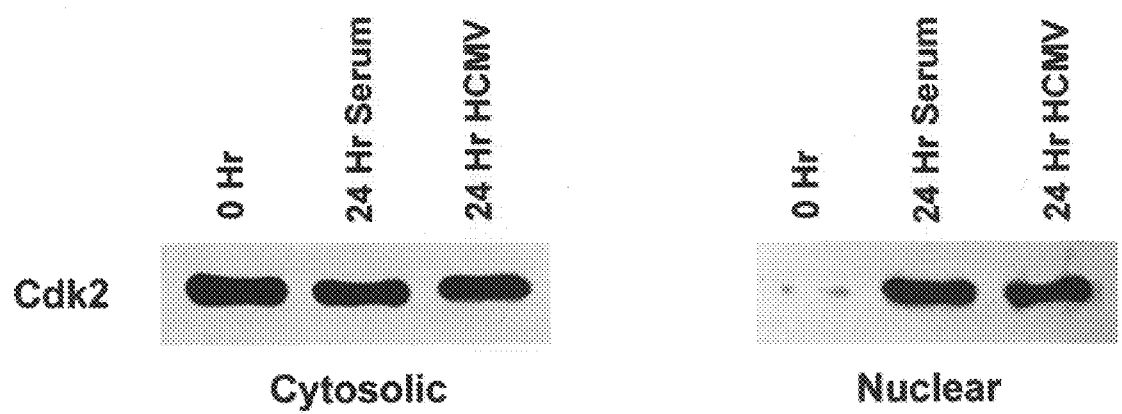
FIG. 6. Subcellular localization of Cdk2 in serum-arrested cells following serum-stimulation or HCMV-infection. LU cells were growth arrested by serum-deprivation at subconfluent densities for 48 hr. Cells were then stimulated with 20% FBS or infected with HCMV for 24 hr as described. Cytosolic and nuclear fractions were prepared. Aliquots of each fraction were resolved by SDS-PAGE, transferred to nitrocellulose membrane, and probed with Cdk2 antibody. The abundance of Cdk2 in both nuclear and cytosolic fractions in quiescent cells (0 hr) and 24 hr after serum stimulation or HCMV-infection are shown.

Cells arrested in G0 (0 hr) by serum deprivation exhibited a diffuse cytoplasmic immunofluorescence, with little or no nuclear staining. HCMV-infected or serum-stimulated cells exhibited a diffuse cytoplasmic staining pattern and intense nuclear immunofluorescence. These results suggest that HCMV, like serum, is capable of dramatically increasing the abundance of nuclear Cdk2 within 24 hr post-infection, at which time cyclin E/Cdk2 activity is maximal. Subcellular fractionation was carried out to confirm the immunocytochemical data. Nuclear and cytosolic fractions were prepared, as previously described (Bresnahan et al., 1996b), from subconfluent, serum-arrested cells and from cells that had been HCMV-infected or serum-stimulated for 24 hr. The abundance of Cdk2 present in these fractions were measured by western blotting as shown in FIG. 6.

Very little Cdk2 was detected in the nuclear fraction of serum-arrested cells (0 hr), whereas the amount of nuclear Cdk2 increased dramatically in both HCMV-infected and serum-stimulated cells by 24 hr (FIG. 19B). These results confirm the inmmunocytochemical data and demonstrate that HCMV (like serum) is capable of altering the subcellular localization of Cdk2 in serum-arrested, subconfluent cells.

HCMV, but not serum, is also capable of activating cyclin E/Cdk2 kinase in contact-inhibited cells. Accordingly, the inventors determined if Cdk2 was sequestered in the cytoplasm of cells arrested in G0 by contact inhibition, and, if it was, if HCMV infection would cause translocation of Cdk2 into the nucleus. LU cells were cultured on glass coverslips and allowed to proliferate until the cells became confluent. The density-arrested cells were then fixed for immunofluorescence, infected with HCMV or stimulated with fresh EMEM containing 10% FBS, as described previously (Bresnahan et al, 1996a). The cells were washed 24 hr later, and fixed for immunofluorescence as described above.

Cells arrested in G0 by contact inhibition demonstrated a diffuse cytoplasmic staining pattern with Cdk2 antibodies. Little or no Cdk2 was detected in the nuclei of these cells. Contact-inhibited cells that were HCMV-infected or treated with serum were also stained for Cdk2. Cells treated with 10% FBS showed diffuse cytoplasmic staining with little or no nuclear staining, similar to that seen in untreated cells. However, cells infected with HCMV demonstrated an intense nuclear staining.

Subcellular fractionation was done to confirm the inventors' immunocytochemical data. Contact-arrested LU cells were infected with HCMV or treated with 10% FBS for 24 hr as described above. Nuclear and cytosolic fractions were prepared, and Cdk2 abundance was determined by western blotting. In contact-arrested LU cells, Cdk2 was predominantly located in the cytosolic fraction; and very little Cdk2 was contained within the nuclear fraction. Similar results were obtained for contact-arrested cells that had been treated with 10% FBS for 24 hr. HCMV infection resulted in a large increase in the abundance of Cdk2 in the nuclear fraction. These results confirmed the immunocytochemical data, showing that Cdk2 is predominantly located within the cytoplasm of contact-arrested cells. However, HCMV infection, but not serum growth factors caused a dramatic increase in the abundance of Cdk2 in the nuclei.

These recent findings suggest that the replication of HCMV depends upon the ability to activate cyclin E/Cdk2 kinase activity. If so, inhibition of Cdk2 activation should inhibit HCMV replication.

Activation of Cyclin E/Cdk2 by HCMV

Figure 7A:
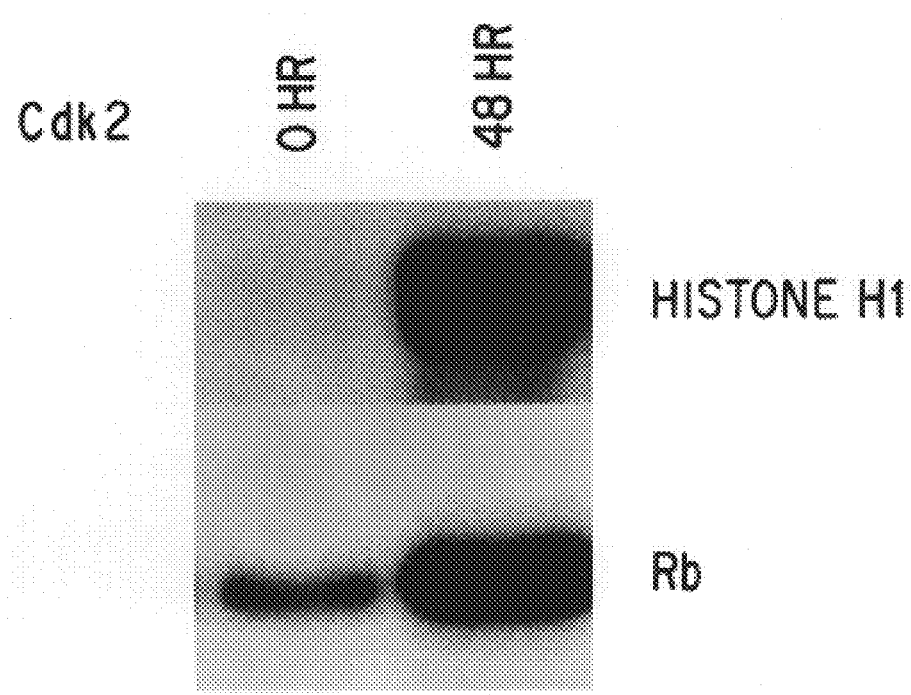
FIGS. 7A–7B. Cdk2 activation in HCMV-infected cells. LU cells were growth arrested by contact inhibition and infected with HCMV as described in the Materials and Methods. Prior to infection (0 Hr) or 48 hr post-infection cells were harvested and equal amounts (100 $\mu$g) of cell lysates immunoprecipitated with Cdk2 antibody. The resulting immunoprecipitates were assayed for kinase activity using either Rb or histone H1 as a substrate as described in the Materials and Methods (FIG. 7A). Cell lysates were also immunoprecipitated with either cyclin E or cyclin A antibodies and assayed for kinase activity using histone HI as a substrate (FIG. 7B).
Figure 7B:
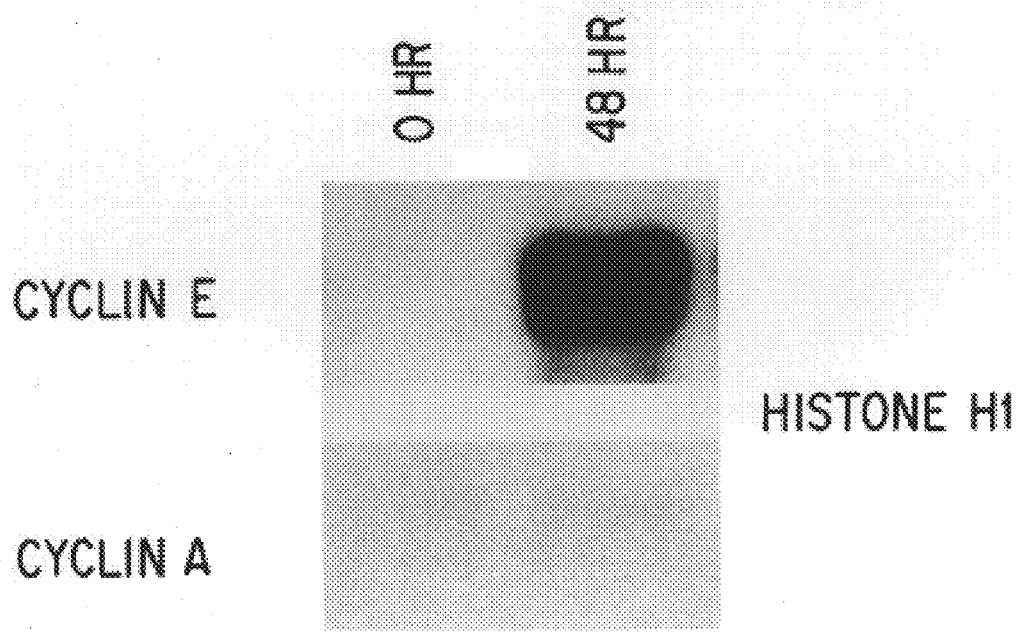

The data shown in FIGS. 7A–7B illustrate HCMV's ability to activate Cdk2. LU cells were arrested by contact-inhibition and then infected with HCMV. Cell lysates were prepared before infection (0 hr) and 48 hours post-infection and assayed for Cdlk kinase activity. FIG. 7A shows that HCMV-infection results in a dramatic increase in Cdk2 kinase activity using both histone HI and Rb as substrates. Kinase assays were also done on cyclin E and cyclin A immunoprecipitates from HCMV-infected cells. HCMV-infection resulted in an increase in cyclin E kinase activity with no induction of cyclin A kinase activity (FIG. 7B). These results demonstrate that the Cdk2 activity that is induced in HCMV-infected cells is due to cyclin E/Cdk2 complexes and not cyclin A/Cdk2 complexes (Bresnahan et al., 1996a).

Roscovitine Inhibits HCMV Replication.

Figure 8A:
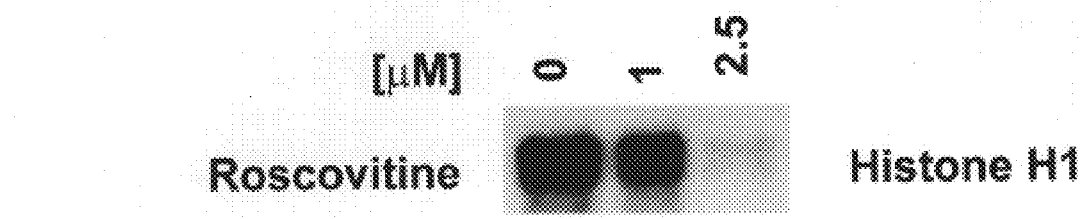
FIGS. 8A–8D. Inhibition of cyclin E/Cdk2 activity, HCMV DNA synthesis and virus yields by roscovitine. LU cells were growth arrested by contact inhibition and infected with HCMV. 48 hr post-infection cell lysates were prepared and 100 $\mu$g of total protein was immunoprecipitated with cyclin E antibody and in vitro kinase activity determined in the presence of the indicated concentration of roscovitine (FIG. 8A). Cells were also infected and treated with various concentrations of roscovitine following infection. 72 hr post-infection, the cells were harvested, total DNA isolated, and the abundance of HCMV DNA determined by slot blot hybridization using a specific HCMV DNA probe (FIG. 8B). 96 hr post infection, infected cells were lysed by freeze-thaw, followed by sonication. Cellular debris was removed by sedimentation and the HCMV containing superatants were assayed for infectivity by plaque assay as described in the Materials and Methods (FIG. 8C). Values represent the average of three independent experiments with standard errors shown.

The inventors used an inhibitor of Cdk2 activity, roscovitine. to determine that Cdk2 activity is necessary for HCMV replication. The $IC_{50}$ for cyclin E/Cdk2 inhibition in vitro by roscovitine is 0.71 $\mu$M (Meijer, 1996; Rudolph et al., 1996). The inventors determined that roscovitine could inhibit cyclin E/Cdk2 activity from HCMV-infected cells at similar concentrations. Cell lysates were prepared from LU cells that had been infected with HCMV for 48 hr and assayed for cyclin E/Cdk2 kinase activity in the presence of various concentrations of roscovitine. FIG. 8A shows that roscovitine inhibited cyclin E/Cdk2 kinase activity in a dose-dependent manner with cyclin E/Cdk2 activity being inhibited by greater than 95% at 2.5 $\mu$M.

Figure 8B:
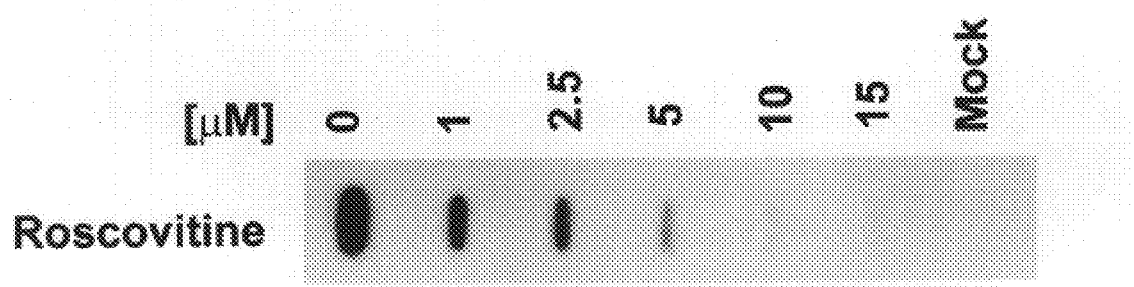
Figure 8C:
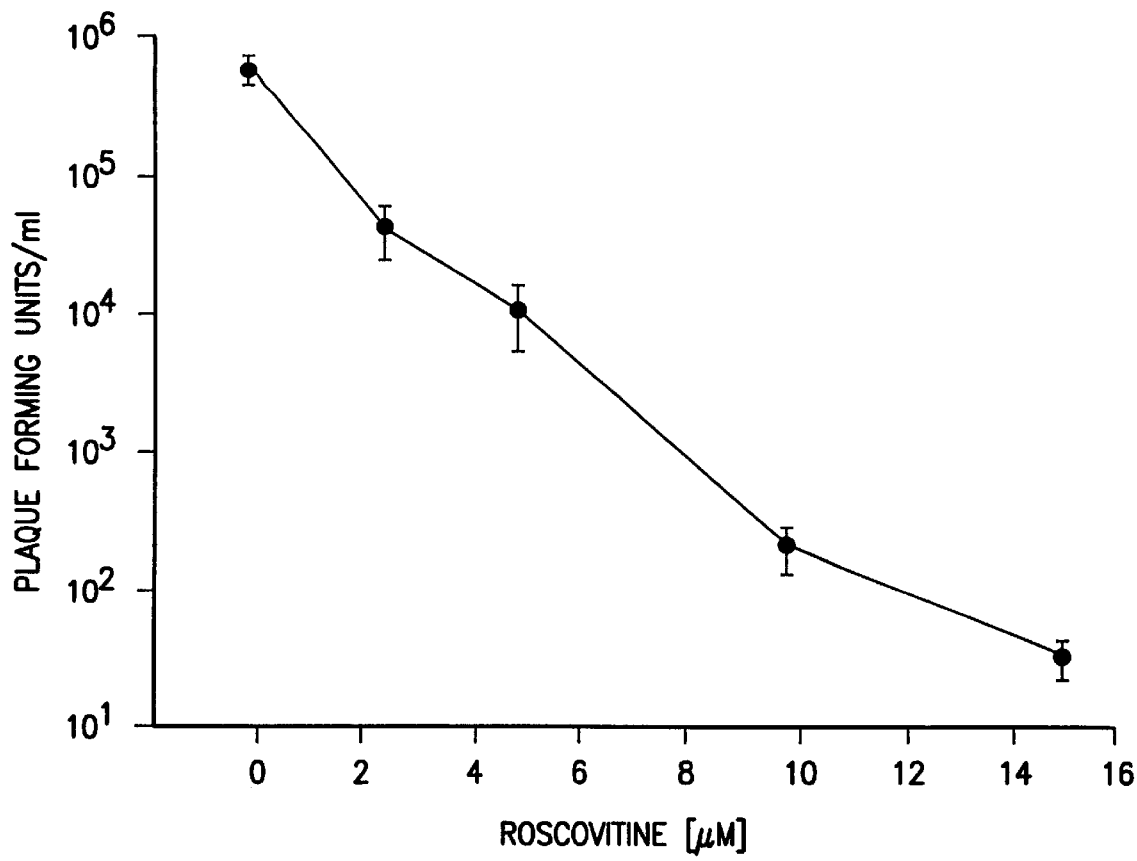

The inventors also determined if roscovitine could inhibit accumulation of HCMV DNA in a dose-dependent manner after addition to infected LU cells. Density-arrested LU cells were infected for 1 hour after which the virus inoculum was removed and replaced with medium containing various concentrations of roscovitine. Total DNA was isolated from LU cells that had been infected for 72 hr, and the abundance of HCMV DNA was determined by slot blot hybridization. As FIG. 8B shows, HCMV DNA abundance was reduced by ~50% in the presence of 1 µM roscovitine; and viral DNA abundance was reduced by >90% by 10 µM inhibitor. Consequently, roscovitine significantly reduced the production of infectious HCMV progeny, as shown in FIG. 8C. Infectious HCMV yields were reduced by >90% after addition of 2.5 µM roscovitine, and >99.9% inhibition occurred at 10 µM.

Figure 8D:
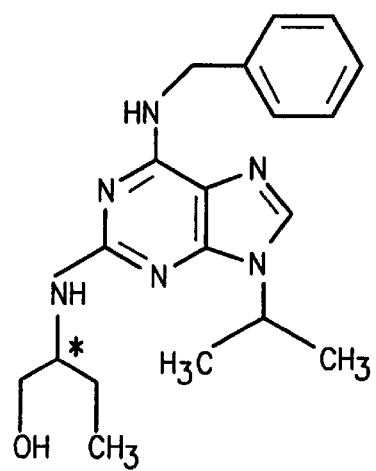

Since the $IC_{50}$ for roscovitine inhibition of Cdk2 in vitro is 0.7 µM (Meijer, 1996; Rudolph et al., 1996), the observation that both viral DNA synthesis and production of infectious virus particles is inhibited 50% at about 1 µM roscovitine suggests that inhibition of Cdk2 accounts for inhibition of viral DNA replication. The chemical structure of roscovitine is shown in FIG. 8D.

Figure 9A:
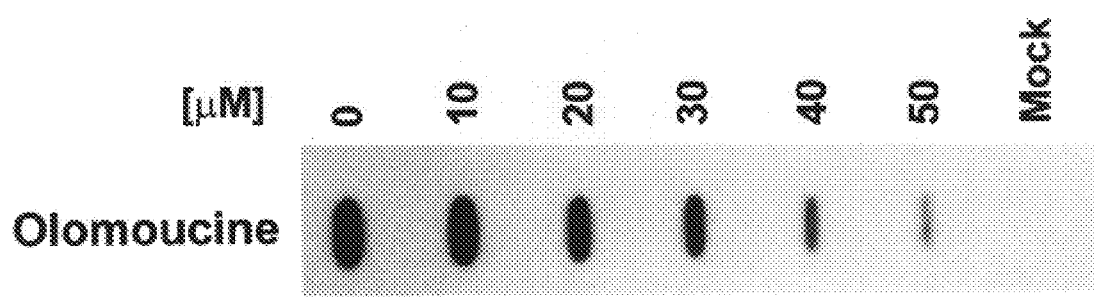
FIGS. 9A–9C. Inhibition of HCMV DNA synthesis and virus yields by olomoucine. LU cells were growth arrested by density-arrest. Cells were infected and treated with various concentrations of olomoucine following infection. 72 hr post-infection, the cells were harvested, total DNA isolated, and the abundance of HCMV DNA determined by slot blot hybridization using a specific HCMV DNA probe (FIG. 9A). 96 hr post infection, infected cells were lysed by freeze-thaw, followed by sonication. Cellular debris was removed by sedimentation and the HCMV containing supernatants were assayed for infectivity by plaque assay as described in the Materials and Methods (FIG. 9B). Values represent the average of three independent experiments with standard errors shown.
Figure 9B:
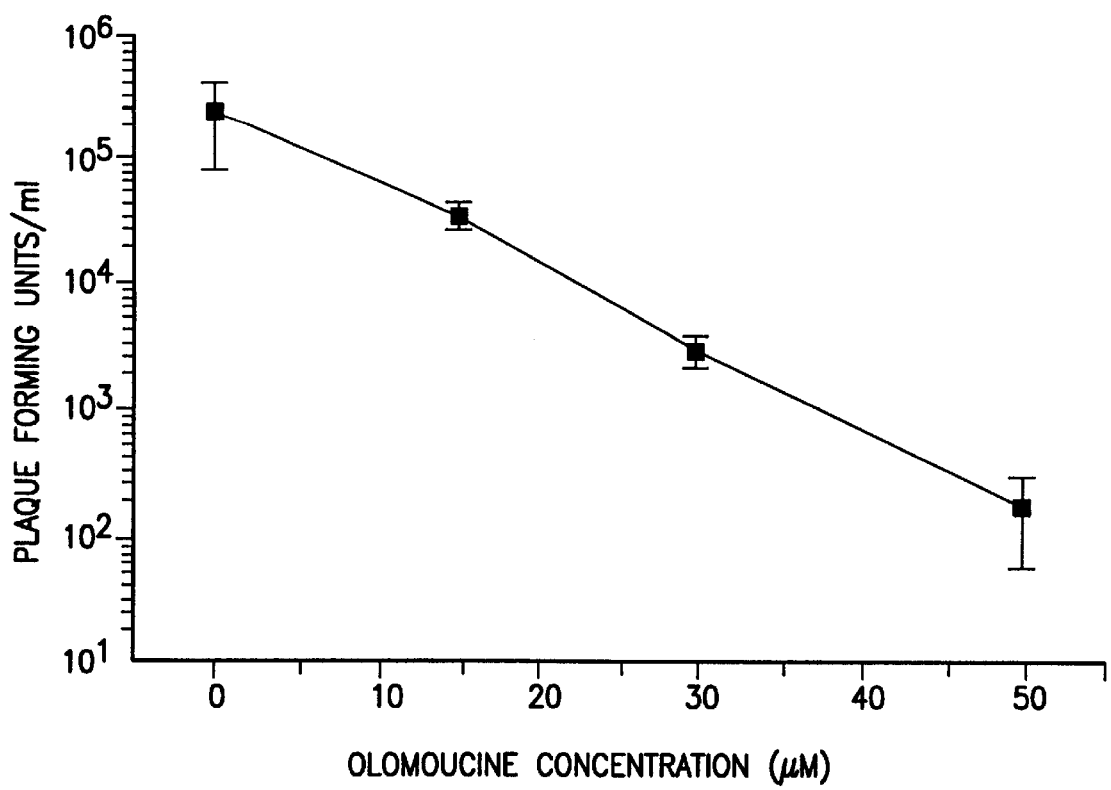
Figure 9C:
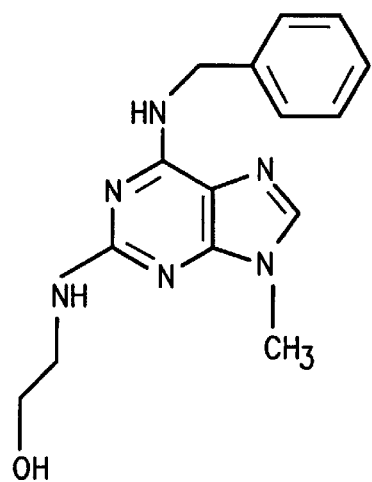

Similar results were obtained when olomoucine, a Cdk2 inhibitor that is structurally related to roscovitine (Meijer, 1996). was used (FIGS. 9A–9C); however, the concentration of olomoucine that was required to inhibit viral DNA synthesis and virus yield was about 10-fold higher than the corresponding concentration of roscovitine. The $IC_{50}$ for olomoucine-mediated inhibition of Cdk2 in vitro is 7 µM. (Vesely et al., 1994) 1 0-fold higher than that of roscovitine. The chemical structure of olomoucine is shown in FIG. 9C. Those of skill in the art will thus understand that any inhibitor of Cdk2 should inhibit viral DNA replication. From these results, it is clear that any newly developed Cdk2 inhibitor will inhibit replication of any viral DNA dependent on cell replication.

Figure 10A:
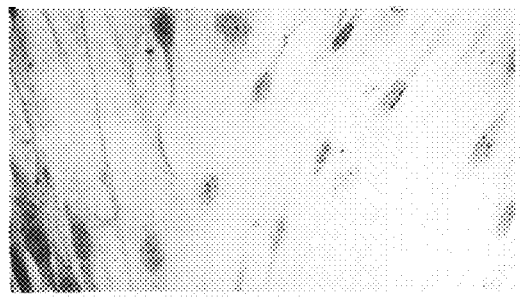
FIGS. 10A–10D. Hematoxylin and eosin staining of HCMV-infected cells treated with roscovitine. LU cells were treated with 15 $\mu$M roscovitine for 96 hr and stained with hematoxylin and eosin as described in the Materials and Methods (FIG. 10A). LU cells were also infected with HCMV and treated with either 0 $\mu$M (FIG. 10B), 5 $\mu$M (FIG. 10C), or 15 $\mu$M (FIG. 10D) roscovitine following infection. Infected cells. were harvested 96 hr post-infection and stained with hematoxylin and cosin.
Figure 10B:
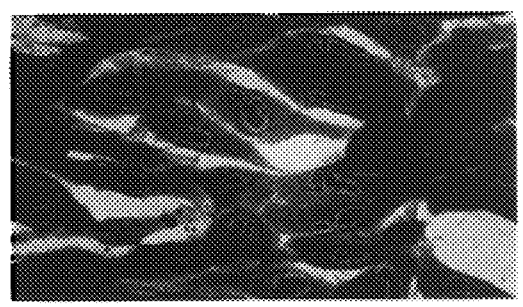
Figure 10C:
Figure 10D:
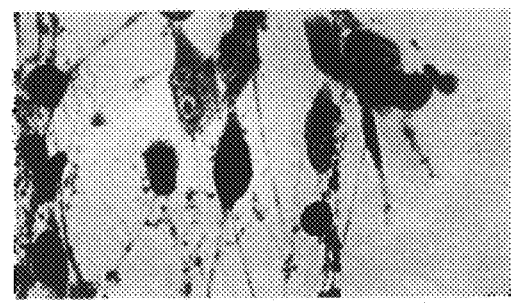

Hematoxylin and eosin staining was also done on non-infected and infected cells both in the absence and presence of roscovitine. Non-infected cells were treated with 15 µM roscovitine for 96 hr and subsequently stained with hematoxylin and eosin. FIG. 10A demonstrates that non-infected LU cells treated with roscovitine show no morphological changes. Infected cells were also stained 96 hr post-infection and examined for morphological changes. As FIG. 10B shows, infected, untreated cells were flat in shape and displayed large nuclear inclusions characteristic of HCMV infection. In the presence of 5 µM roscovitine the infected cells were rounded and appeared to be undergoing cell death. However, even in the presence of 5 µM roscovitine small nuclear inclusions are evident indicating that the cells are infected (FIG. 10C). Cells infected and treated with 15 µM roscovitine were clearly dying or dead by 96 hr after infection (FIG. 10D). Similar morphological changes were observed for cells infected and treated with olomoucine. These results suggest that HCMV-infected cells treated with inhibitors of Cdk2 activity undergo cell death that does not result from treatment with inhibitor alone.

Figure 11B:

To determine whether drug-associated cellular toxicity was responsible for the reduced HCMV replication, the inventors investigated the effects of both roscovitine and olomoucine on non-infected cells. Non-infected cells treated with 15 µM roscovitine for 96 hr were arrested in G0/G1 or G2/M phase (FIG. 11A) and did not present with any obvious morphological changes (FIG. 11A). In addition, more than 70% of the cells that had been exposed to roscovitine or olomoucine in this fashion were able to incorporate bromodeoxyuridine (BrdU) within 24 hr after removal of the inhibitor (FIG. 11B). Similar result were obtained when roscovitine- or olomoucine-treated cells were analyzed for cell cycle progression (using flow cytometry) after removal of the drug (FIG. 11A).

The results herein, including those shown in FIGS. 8 and 10, are consistent with the hypothesis that roscovitine, like PAA, blocks viral DNA replication at some point after expression of immediate early genes but prior to the initiation of the late phase of HCMV replication. This effect can be demonstrated in at least two cell lines that are know to be productive for HCMV infection.

Figure 12:
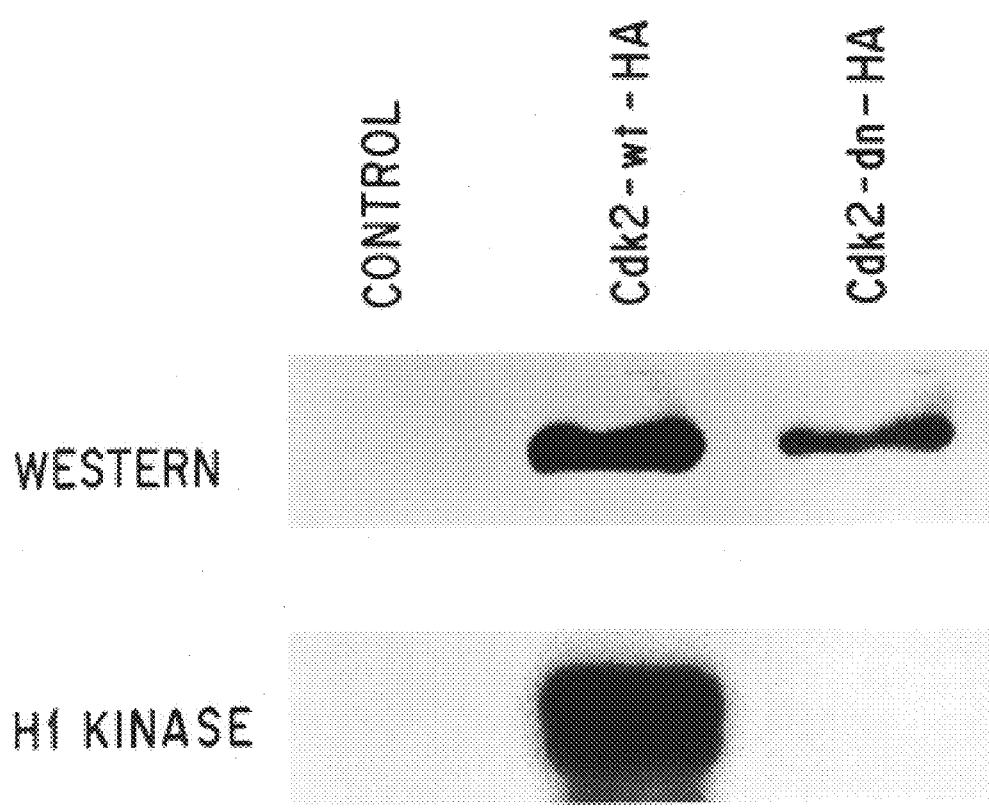
FIG. 12. Expression and activity of wild-type and dominant negative Cdk2. U-373 cells were transiently transferred with either HA-tagged wild type Cdk2 (Cdk2-wt-HA) or dominant negative Cdk2 (Cdk2-dn-HA). Cells were then harvested 48 hr later and assayed for HA expression (Western) and HA-associated kinase activity (H1 Kinase).

Both roscovitine and olomoucine inhibit Cdk1, as well as Cdk2 (Meijer, 1996: Vesely et al., 1994). Both Cdk1 and Cdk2 are inhibited at similar concentrations of roscovitine, and inhibition of HCMV replication could have been due to inhibition of either enzyme. A previously characterized dominant negative Cdk2 mutant (van den Heuval and Harlow, 1993) was used to show that the effects of roscovitine on HCMV replication are due to inhibition of Cdk2. This predicts that expression of the dominant negative Cdk2, which results in inhibition of Cdk2 activity (van den Heuval and Harlow, 1993), should be sufficient for inhibition of HCMV replication. U-373 cells were used in these studies because of the low efficiency of transfection of LU cells. U-373 cells were transiently transfected with expression vectors encoding hemagglutinin (HA)-tagged wild-type Cdk2 (pCMVCdk2-wt-HA) or HA-tagged dominant negative Cdk2 (pCMVCdk2-dn-HA). The hemagglutinin tag allowed the inventors to distinguish between endogenous and exogenous Cdk2 by the use of specific hemagglutinin antibodies. Cells were harvested 48 hours after transfection and assayed for Cdk2-wt-HA and Cdk2-dn-HA expression and kinase activity. Western blotting with HA antibody showed that cells transfected with either wild-type or dominant negative Cdk2 expressed the exogenous protein (FIG. 12). Histone H1 kinase activity was associated with Cdk2 wild-type HA immunoprecipitates but not with the Cdk2 dominant negative HA precipitates (FIG. 12).

Figure 13A:
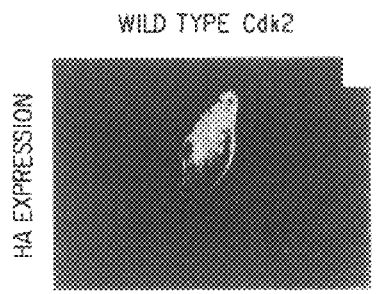
FIGS. 13A–13D. Inhibition of HCMV late antigens in cells expressing dominant negative Cdk2. U-373 cells were transiently transferred with either HA-tagged wild type Cdk2 (Cdk2 wild type) or dominant negative Cdk2 (Cdk2 dominant negative). Cells were then seeded onto glass cover slips and infected with HCMV 24 hr after transfection. The cells were fixed 72 hr post-infection with acetone:methanol (1:1) and dual immunofluorescent staining was done for HCMV UL80.5 (Rhodamine) and HA (FITC) expression.
Figure 13B:
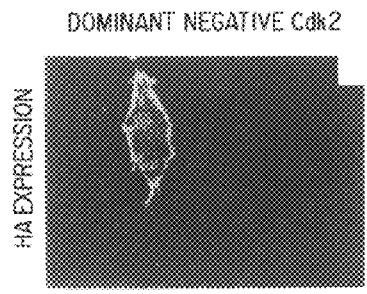
Figure 13C:
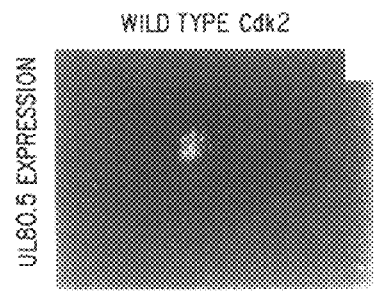
Figure 13D:
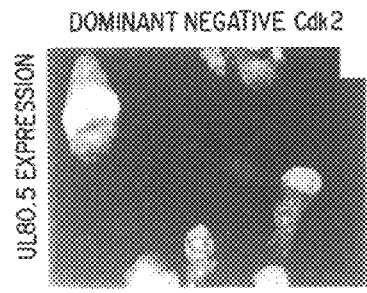

To determine if Cdk2 activity is required for HCMV replication, dual immunofluorescent staining was used to assay for expression of the HA-tagged Cdks and for the HCMV late antigens encoded by UL80.5, in transfected U-373 cells that were also infected with HCMV. As shown in FIGS. 13A–13D, cells that expressed the dominant negative Cdk2 mutant (shown in FIG. 13B) did not express UL80.5 late antigens (FIG. 13D). Cells that expressed wild-type Cdk2 (FIG. 13A) supported viral replication, as evidenced by expression of the UL80.5 late gene products (FIG. 13C). Three independent studies of this kind were done; and the percentage of infected cells, cells expressing Cdk2-wt-HA plus UL80.5, or cells expressing Cdk2-dn-HA plus UL80.5 were determined. Transfection efficiencies were similar for both wild type and dominant negative Cdk2. About 33% of the cells in the infected cultures expressed UL80.5 late antigens. This efficiency of infection was observed irrespective of whether the cells were transfected with wild type or dominant negative derivatives of Cdk2. The susceptibility of U-373 cells to HCMV in the inventors studies is consistent with published data (Ripalti et al., 1995). The efficiency of transient expression of Cdk2 derivatives is much lower than the frequency of virus infection. The inventors estimate that <5% of the U-373 cells. and therefore <5% of the infected cells, express either HA-tagged Cdk2 derivatives. Similar results were obtained with β-galactosidase expression vectors. Nevertheless, as Table 3 shows, about 37% of the cells that expressed the wild type HA-tagged Cdk2 derivative also expressed UL80.5 late antigens. This observation demonstrates that transient expression of HA-tagged wild type Cdk2 derivative has no significant effect on viral replication, as assessed by expression of viral late antigen. On the other hand, only 2% of cells that expressed the dominant negative Cdk2 mutant also expressed UL80.5 late antigens (p<0.0001). This observation indicates that Cdk2 activity is vital for HCMV replication and inhibition of Cdk2 is sufficient to inhibit viral replication.

Table 3 shows the percent of cells expressing Cdk2-HA and HCMV UL80.5 antigens. U-373 cells were transiently transfected with HA-tagged wild type or dominant negative Cdk2 and subsequently infected with HCMV. The percent of infected cells was determined by measuring expression of HCMV UL80.5 antigens. Multiple random fields were counted to accumulate about 150 total cells, of which about one-third expressed UL80.5. The percent of cells expressing UL80.5 antigens was also determined from cells expressing HA-tagged wild type or dominant negative Cdk2. In this case, multiple fields were counted to accumulate about 150 HA-positive cells, which were scored for expression of UL80.5. Statistical significance was estimated by Student's t-test, comparing infected cells expressing HA to the percent infected cells in the cultures.

TABLE 3

Percent of Cells Expressing Cdk2-HA and HCMV UL80.5 Antigens

| Cells Expressing | Study 1 | Study 2 | Study 3 | Mean % (±s.d.) |
| --- | --- | --- | --- | --- |
| UL80.5 Antigens | 52/156 | 46/156 | 53/150 | 33 (±2) |
|  | 33% | 30% | 35 |  |
| pCMVCdk2-wt-HA + UL80.5 Antigens | 58/148 | 56/154 | 53/147 | 37 (±1) |
|  | 39% | 37% | 36% | p > 0.05 |
| pCMVCdk2-dn-HA + UL80.5 Antigens | 3/151 | 5/161 | 4/159 | 26 (±0.6) |
|  | 2% | 3% | 3% | p < 0.0001 |

An important aspect of the present studies concerns mechanisms involved in regulating G1 cyclins, Cdks, and CKIs, along with the effects HCMV infection has on these regulatory proteins. The inventors' initial studies were undertaken to determine the mechanisms that govern activation of cyclin E kinase during transition from the G0 state into S phase. To this end the inventors have focused attention upon those principles felt most likely to play a direct role in determining the activity of the cyclin E/Cdk2 complex. These principles include Cdk2, cyclin E, and the Cip1 family of CKIs. The inventors' propose that the activity of cyclin E/Cdk2 kinase should reflect the relative abundance of these entities, their subcellular localization, and the abundance and/or activity of other factors that might influence the ability of cyclin E to associate with Cdk2 and form active complexes.

Although there is abundant cyclin E and Cdk2 in G0 cells, these two proteins do not reside in the same subcellular compartment. Consequently, quiescent cells contain very low concentrations of cyclin E/Cdk2 complexes. The inventors have reasoned that sequestration of the catalytic and regulatory subunits is the primary mechanism whereby activation of cyclin E-dependent kinase is precluded in G0.

A most significant aspect of this research has focused on the effects HCMV has on cell cycle progression and genes regulating entry into S phase. In certain respects, HCMV and serum growth factors exhibit similar effects upon cell cycle progression. However, important differences were also noted. One of the most striking differences has to do with replication of cellular DNA. HCMV-infected cells exhibit a significant increase in total DNA content, but this increase in DNA content is due almost entirely to accumulation of viral DNA. The inventors' conclusions, in this respect, differ from those reached by another group, which reported that productive HCMV infection caused replication of the cellular genome and G2/M arrest (Jault et al., 1995). However, this conclusion was based upon the results of flow cytometry analyses, which cannot discriminate between viral and cellular DNA.

The inventors are also confident that many of the discrepancies between the results obtained by Jault et al., and the inventors' results have to do with the fact that their infection protocol involved prolonged exposure of serum-starved, subconfluent cells to serum growth factors that were present in the medium that they used to maintain the cells after viral infection. For example, they observed induction of cyclin E and cyclin A, as well as cell cycle progression from G0 into S phase, in mock-infected cells.

These observations are entirely consistent with serum stimulation of growth factor-deprived, subconfluent cells. The inventors' protocol involves maintenance of infected subconfluent cells in serum-free, spent medium. This procedure precludes serum stimulation; and neither induction of G1 cyclins, nor activation of cellular DNA synthesis, nor cell cycle progression was observed in mock-infected cells under the conditions that the inventors have employed. The inventors have taken great care to avoid such complications as are likely to result from simultaneous infection and serum-stimulation of subconfluent cells. Furthermore, the inventors have extended studies to include density-arrested cells, which are refractory to serum growth factors, but not to viral infection.

The absence of cellular DNA synthesis in HCMV-infected cells could be due to viral inhibition of some essential pathway that leads to S phase. Alternatively, the virus may selectively activate pathways that lead to activation of precursor biosynthesis, while failing to activate pathways that lead to host cell DNA replication. The inventors' data strongly suggest that failure to induce cyclin A and consequent failure to activate cyclin A-dependent kinase may be the proximal impediments to host cell DNA synthesis in HCMV-infected cells. There is abundant evidence to support the proposition that, failing to activate cyclin A, a cell will not replicate its DNA (Resnitzky et al., 1995; Girard et al., 1991).

The early events that occur after HCMV infection share many aspects in common with the cellular response that is provoked by addition of growth factors to serum-starved cells (reviewed in Albrecht et al., 1992), and the data suggest that the virus elicits a general pattern of cellular activation that is characteristic of cell division cycle progression through late G1. As do serum growth factors, HCMV induces cyclin E and activates cyclin E kinase. HCMV infection also results in the translocation of Cdk2 into the nucleus upon infection of either serum-arrested or density-arrested cells. The virus likewise promotes hyperphosphorylation of the retinoblastoma susceptibility gene product.

The HCMV induction of cyclin E-dependent kinase activity is due, at least in part, to an increase in the abundance of cyclin E protein. However, cyclin E/Cdk2 kinase is activated later and remains activated longer than one might expect if its activity were a simple function of cyclin E abundance. The delay in activation of cyclin E/Cdk2 and the persistence of kinase activity appear to be due to the effects of the two major Cdk2 inhibitory subunits, Cip1 and Kip1. Cip1 and Kip1 are abundant in serum- and density-arrested LU cells, and it is probable that the lag that one observes between induction of cyclin E and activation of cyclin E/Cdk2 kinase reflects the length of time required to accumulate sufficient complex to exceed the CK1 threshold. The virus also inhibits the expression of both Cip1 and Kip1, which decreases the cyclin kinase inhibitor threshold and permits cyclin E/Cdk2 complexes to remain active at later times during infection when the amount of cyclin E is actually decreasing. Maximum viral DNA synthetic activity occurs about 72 hr after infection, and persistent activation of cyclin E/Cdk2 may serve to insure that activation of precursor biosynthetic pathways is sustained during the most active period of viral DNA replication.

Since neither cyclin D nor cyclin A are induced by HCMV, it appears that phosphorylation of pRb is due to cyclin E/Cdk2 kinase. This idea is supported by the data which indicates the phosphorylation pattern of Rb following HCMV infection is different from that observed following serum stimulation. Phosphorylation of pRb during G1 by Cdk2 releases, and thereby activates, a large number of cellular transcription factors, of which members of the E2F family are prototypic (Faroham et al., 1993; Nevins, 1992). E2F family members stimulate transcription of a large number of genes, including nucleotide biosynthetic genes such as dihydrofolate reductase, thymidine kinase, thymidylate synthase, and ribonucleotide reductase (see Ohtani et'al., 1995 and references therein). Dihydrofolate reductase and thymidine kinase are known to be induced by HCMV (Wade et al., 1992; Estes and Huang, 1977). In the case of dihydrofolate reductase, activation by HCMV requires E2F in combination with an HCMV immediate early gene product IE72 (Margolis et al., 1995). HCMV also activates c-myc (Boldogh et al., 1990; Monick et al., 1992; Colberg-Poley and Santomenna, 1988), which may be a target for E2F transcription factors under some conditions (Hamel et al., 1992). c-MYC, in turn, activates the genes encoding ornithine decarboxylase (Bello-Femandez et al., 1993), leading to polyamine synthesis, and carbamoyl phosphate synthetase/aspartate transcarbamylase/dihydroorotase (CAD) (Miltenberger et al., 1995), which catalyzes the committed reaction in pyrimidine biosynthesis. All of these responses are characteristic of the late G1/early S phase transition. Stated another way, all of these responses to HCMV serve to prime the cell for DNA synthesis.

Integrity of the viral genome is essential to activation of cyclin E, which the inventors consider to be an essential manifestation of the virus' ability to push cells into late G1. The inventors' working hypothesis is that one or more of the viral gene products provides this function. The inventors do not know if the virus fails to activate cyclins A and/or D during productive infection, or if the virus encodes some principle that directly blocks induction of these cyclins. The observation that abortive infection. in which the full complement of viral genes is not expressed, allows for cellular DNA replication is consistent with the latter proposition; but no experimental data are available at this time. The inventors suspect that failure to activate cyclin A, with attendant failure to initiate host cell DNA replication, is also a critical feature of the viral life cycle. The inventors propose that activation of cyclin E, along with induction of c-MYC, establishes an environment in which precursors for macromolecular biosynthesis are abundant (i.e., a state resembling late G1); whereas failure to activate cyclin A, and concomitant failure to initiate host cell DNA synthesis, assures that the virus will have uncompeted access to these essential macromolecular precursors.

All of these observations indicate that cyclin E/Cdk2 activity is necessary for efficient HCMV replication. Inhibition of Cdk2 activity by drugs or dominant negative inhibitors block HCMV replication. Inhibition of Cdk2 activity by the chemical inhibitors roscovitine, olomoucine or other Cdk2 inhibitors inhibit HCMV DNA synthesis, production of infectious progeny, and late antigen expression. The data indicate that Cdk2 activity is required after expression of HCMV immediate early gene expression but prior to the initiation of HCMV DNA synthesis. It will be interesting to further investigate the exact role Cdk2 activity plays in HCMV replication. A more complete understanding of the interactions of HCMV and cellular processes required for viral replication, should lead to the development of even more effective means to control HCMV infection. The use of Cdk2 inhibitors such as roscovitine and olomoucine, for example provides novel drugs to help fight HCMV infection. Thus, inhibitors of Cdk2, in pharmaceutically acceptable carriers, may be administered in prophylactically or therapeutically effective amounts to patients to prevent or treat infection by DNA viruses.

As used herein, "pharmaceutically acceptable carrier" includes any and all solvents, dispersion media, coatings, antibacterial and antifungal agents, isotonic agents and the like. The use of such media and agents for pharmaceutically active substances is well knoat in the art. Except insofar as any conventional media or agent is incompatible with the active ingredient, its use in the therapeutic composition is contemplated. Supplementarv active ingredients can also be incorporated into the compositions. The phrase "pharmaceutically acceptable" also refers to molecular entities and compositions that do not produce an allergic or other untoward reaction when administered to an animal or a human.

Pharmacologically active compositions of the inhibitors of cyclin E/Cdk2 activity would preferably be introduced directly to the DNA virus or herpesvirus infection as parenteral preparations. The pharmaceutical preparations of inhibitor of cyclin E/Cdk2 activity suitable for injectable use include sterile aqueous solutions or dispersions and sterile powders for the preparation of sterile injectable solutions or dispersions. In all cases the form must be sterile and must be of a viscosity suitable for syringability. It should be stable under the conditions of manufacture and storage and is preferably preserved against the contaminating action of microorganisms, such as bacteria and fungi. The carrier may be a solvent or dispersion medium containing, for example, water, ethanol, polyol (for example, gycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In most cases, it is preferable to include isotonic agents, for example, sugars or sodium chloride. An excipient such as serum albumin may be added to promote stability.

Sterile injectable solutions are prepared by incorporation of the inhibitor of cyclin E/Cdk2 activity or analogs in the required amount in the appropriate solvent with various other ingredients enumerated above, as required, followed by filter sterilization. Generally, dispersions are prepared by incorporating-the various sterilized active ingredients into a sterile vehicle which contains the basic dispersion medium and the required other ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For parenteral administration in an aqueous solution, for example, the solution should be suitably buffered as necessary for the stability of the inhibitor of cyclin E/Cdk2 activity or analog active ingredient and the liquid diluent first rendered isotonic with sufficient saline or glucose. Preferred pH range of the solution will be between 6.5 and 7.5. These particular aqueous solutions are especially suitable for intraperitoneal administration. In this connection, sterile aqueous media which can be employed will be known to those of skill in the art in light of the present disclosure.

The preferred dosage of inhibitor of cyclin E/Cdk2 activity in a parenteral administration will vary, depending upon the extent of the virus infection, the severity of the symptoms associated with the infection and patient age, weight and medical history. The number of administrations of the parenteral composition will also vary according to the response of the individual patient to the treatment. In one exemplary application. the dosage of inhibitor of cyclin E/Cdk2 activity would vary with the type of disease and the route of administration. Further studies with animal models of infection will completely define projected doses. A dose of 3 $\mu$g/kg is tolerated by rate and it is expected that for humans, a roscovitine dose of 1 $\mu$g/kg to 10 $\mu$g/kg will be tolerated and antivirally effective. For example, the dose, to be prophylactically or therapeutically effective should be enough to achieve a 4 $\mu$M to 20 $\mu$M roscovitine concentration in the environment of infected or potentially infected cells. Weaker Cdk2 inhibitors will be needed at higher concentrations, and stronger, at lower.

In other preferred embodiments of the invention, pharmacologically active compositions could be introduced to the patient through transdermal delivery of a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture.

Suitable amounts of active ingredient inhibitor of cyclin E/Cdk2 activity for compositions for topical administration typically may range from 0.1–100 $\mu$g per 1000 g of composition. Administration of the ointments, creams and lotions of this invention may be from between once a day to as often as is necessary to relieve symptoms and will vary according to the strength of the medication, active ingredient, patient age and the severity of the symptoms. Administration of the topical medications of this invention may be directly to the infected area.

Another preferred method of administering pharmacologically active compositions of inhibitor of cyclin E/Cdk2 activity is as an aerosol. Aerosol compositions of the inhibitor of cyclin E/Cdk2 activity of the present invention will be especially useful for the treatment of living tissue. although they could also be used for dermal applications. The term aerosol refers to a colloidal system of finely divided solid of liquid particles dispersed in a liquified or pressurized gas propellant. The typical aerosol of the present invention for oral or nasal inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to patient age, weight and the severity and response of the symptoms.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alberts et al., In: *Molecular Biology of the Cell*, New York, Garland Publishing, 728–738, 1989.

Albrecht et al., *Subcell. Biochem.*, 15:157–202, 1989.

Albrecht et al., *Soc. Invest. Dermal.* 98:295–355, 1992.

Albrecht et al., *Lab. Invest.*, 42:1–7, 1980a.

Albrecht et al., *J. Gen. Virol.*, 51:83–97, 1980b.

Albrecht et al., *J. Gen. Virol.* 30:167–177, 1976.

Albrecht and Weller, *Am. J. Clint. Pathol.*, 73:648–654, 1980.

Alford et al., In: *The human herpesviruses: an interdisciplinary, perspective*, Nalimias et al., eds., New York: Elsevier, 159–171, 1981.

Alford et al., *Reviewed infect. Dis.*, 12:5745–5753, 1990.

AbuBaker et al. *Biocheni. Biophyls. Res. Commun.* 166:953–959, 1990.

Baldin et al., *Genes Dean.* 7:812–821, 1993.

Bello-Femandez et al., *Proc. Natl. Acad. Sci. U.S.A.*, 90:7804–7808. 1993.

Baracchini et al., *Virology*, 188:518–529, 1992.

Bates et al., *Oncogene*, 9:71–79, 1994.

Benson and Huang, *J. Virol.*, 64:9–15, 1990.

Boldogh et al., *Science*, 247:961–964, 1990.

Boldogh et al., *Arch Virol.*, 118: 163–177, 1991.

Boshart et al., *Cell.* 41:521–530, 1985.

Bradford, *Anal. Biochem.*, 72:248–254, 1976.

Brasfield et al., *Pediatrics*, 79:76–83, 1987.

Bresnahan et al., *Virology*, 224:150–160, 1996a.

Bresnahan et al., *Cell Growth & Diff*, 7:1283–1290, 1996b.

Chang et al., *J. Virol.* 63:281–290, 1989.

Cherrington and Mocarski, *J. Virology*, 63: 1435–1440, 1990.

Cherrington et al., *J. Virol.*, 65:887–896, 1991.
Chou, *Reviewed infect. Dis.* 12(suppl):727–736, 1990.
Clarke, *Curr. Biology*, 5:40–42, 1995.
Colberg et al., *Virology*, 166:217–228, 1988.
Collier et al., *Am. J. Med*, 82:593–601, 1987.
DeMarchi, *Virology*, 129:274–286, 1983.
Depto and Stenberg, *J. Virol.*, 63:1232–1238, 1989.
Detels et al., *J. Am. Med Assn*, 251:1719–1722, 1984.
Dieterich et al., *J. Infect. Dis.*, 167:278–282, 1993.
Draetta, *Curr. Opin. Cell Biol.*, 6:842–846, 1994.
Drew et al., *J. Infect. Dis.* 143:188–192, 1981.
Drew et al., *Ann. Intern. Med.* 103:61–63, 1985.
Dulic et al., *Science*, 257:1958–1961, 1992.
Dworsky et al., *Pediatrics*, 72:295–299, 1983.
El-Deiry et al., *Cell*, 75:817–825, 1993.
Elledge and Harper, *Curr. Opin. Cell Biol.*, 6:847–852, 1994.
Estes and liuang, *J. Virol.*, 24:13–21, 1977.
Farnham et al., *Biochim. Biophls. Acta.* 1155:125–131, 1993.
Fesquet et al., *EMBO J.*, 12:3111–3121, 1993.
Fiala et al., *J. Infect Dis.*, 132:421–433, 1975.
Fiala et al. In: Molecular aspects of human cytomegalovirus, Becker and Darai. eds., Berlin, Springer-Verlag, 128–149, 1993.
Fisher and Morgan, *Cell*, 78:713–724, 1994.
Furukawa et al., *Proc. Soc. Exp. Biol. Med.*, 148:211–214, 1975.
Gehrz, *Adv. Pediat.*, 38:203–232, 1991.
Girard et al., *Cell*, 67:1169–1179, 1991.
Gu et al., *Nature* (Lond), 366:707–710, 1993.
Hagemeir et al., *EMBO J.*, 13:2897–2903, 1994.
Harnel et al., *Mol. Cell. Biol.*, 12:3431:3438, 1992.
Hanks, *Proc. Natl. Acad Sci. USA*, 84:388–392, 1987.
Hannon and Beach, *Nature* (Lond), 317:257–261, 1994.
Harper et al., *Mol. Biol. Cell*, 6:387–400, 1995.
Harper et al., *Cell*, 75:805–816, 1993.
Hawley et al., *Am. J. Clin. Pathol.*, 80:874–877, 1983.
Hinds and Weinberg, *Curr. Opin. Genet. Dev,.* 4:135–141, 1994.
Huang and Kowalik, In: Becker and Darai, *Molecular aspects of human cytomegalovirus*, Berlin, Springer-Verlag, 3–45, 1993.
Huang, *J. Virol,.* 16:298–310, 1975a.
Huang, *J. Virol,.* 16:1560–1565, 1975b.
Hunter and Pines, *Cell*, 79:573–582, 1994.
Isom, *J. Gen. Virol,.* 42:265–278, 1979.
Jault et al., *J. Virol,.* 69:6697–6704, 1995.
Kamiya et al., *Arch. Virol.* 89:13 1–144, 1986.
Kanas et al., *Oral Surg. Oral Med. Oral Pathol,.* 64: 183–189, 1987.
Kapasi and Ricc, *J. Virol,.* 62:3603–3607, 1988.
Kato et al., *Mol. Cell. Biol,.* 14:2713–2721, 1994.
Klucher et al., *J. Virol,.* 63:5334–5343, 1989.
Koff et al, *Science* (Washington D.C.), 257:1689–1694, 1992.
Lew et al., *Nature* (Lond.), 11:423426, 1994.
Li et al., *Oncogente*, 9:2261–2268, 1994.
Liu et al., *J. Virol.*, 65:897–903. 1991.
Lorincz and Reed, *Nature*, 307:183–185, 1984.
Malone et al., *J. Virol.*, 64:1498–1506, 1990.
Margolis et al., *J. Virol.*, 69:7759–7767, 1995.
Matsushime et al., *Cell*, 71:323–334, 1992.
Meijer, *Trends in Cell Biol*, 6:393–397, 1996.
Meyer et al., *J. Virol,.* 62:2243–2250, 1988.
Meyerson et al., *Cold Spring Harbor Symp. Quant. Biol.*, LVI: 177–186, 1991.
Meyerson and Harlow, *Mol. Cell. Biol.*, 14:2077–2086, 1994.
Miltenberger et al., *Mol. Cell. Biol.,"* 15:2527–2536, 1995.
Monick et al., *Am. J. Respir. Cell Mol. Biol.* 7:251–256, 1992.
Morgan, *Nature* (Lond), 374:131–134, 1995.
Nakanishi et al., *Proc. Natl. Acad. Sci. USA*, 92:4352–4356, 1995.
Navia et al., *Ann. Neurol.*, 19:525–535, 1986.
Nelson et al., *Virology* 165:286–290, 1988.
Nevins, *Nature*, 258:424–429, 1992.
Nishiyama et al., *Virology*, 124:221–231, 1983.
Nurse and Bisset, *Nature*, 29:558–560, 1981.
Ohtani et al., *Proc. Natl. Acad. Sci. USA*, 92:12146–12150, 1995.
Ohtsubo et al., *Mol. Cell. Biol.*, 15:2612–2624, 1995.
Pass et al., *Pediatrics* 66:758–762, 1980.
Polyak et al., *Cell* 78:59–66, 1994.
Quelle et al., *Genes Dev.* 7:1559–1571, 1993.
Quinn et al., *J. Am. Med. Assn.*, 257:2617–2621, 1987.
Re et al., *J. Gen. Virol,.* 66:2507–2511, 1985.
Resnitzky and Reed, *Mol. Cell. Biol.*, 15:3463–3469, 1995.
Resnitzky et al., *Mol. Cell. Biol.*, 15:4347–4352, 1995.
Reynolds et al., *N. Engl. J. Med.*, 289:1–5, 1973.
Rice et al., *Proc. Natl. Acad Sci. USA*, 81:6134–6138, 1984.
Ripalti et al., *J. Virol.*, 69:2047–2057, 1995.
Roizman and Sears, In.: Fields. and Knipe, *Fundamental Virology*, New York, Raven Press, Ltd., 849–895, 1991.
Rosenblatt et al., *Proc. Natl. Acad. Sci. USA*, 89:2824–2828, 1992.
Rubin and Tolkoff-Rubin, In: *Progress in transplantation*, Morris and Tilney, eds. Vol 1. Edinburgh: Churchhill Livingstone, 89–114, 1984.
Rubin, *Reviewed infect. Dis.*, 12:S754–S766, 1990.
Rudolph et al., *EMBO J.*, 15:3065–3075, 1996.
Said et al., *Ann. Neurol,.* 29:139–146, 1991.
Sambucetti et al., *EMBO J.*, 8:4251–4258, 1989.
Schooley, *Reviewed infect. Dis,.* 12:8811–8819, 1990.
Schulze et al., *Proc. Natl. Acad. Sci. USA*, 92:11264–11268, 1995.
Serrano et al., *Nature* (Lond.), 336:704–707, 1993.
Sherr, *Cell* 73:1059–1065, 1993.
Sherr, *Cell* 79:551–555, 1994.
Sherr and Roberts, *Genes Dev.* 9:1149–1163, 1995.
Sing and Gamett, *J. Med. Virol.* 14:363–371, 1984.
Slingerland et al., *Mol. Cell. Biol.*, 14:3683–3694, 1994.
Smith and Brennessel, *Infect. Dis. Clinics of N. Amer.*, 8:427–438, 1994.

St. Jeor and Hutt, *J. Gen. Virol.*, 37:65–73, 1977.
Stagno et al., *N. Engl. J. Med.*, 302:1073–1076, 1980.
Staprans et al., *J. Virol.*, 62:3463–3473, 1988.
Stenberg et al., *J. Virol.*, 64:1556–1565, 1990.
Stinski, In: Fields and Knipe, *Fundamental Virology*," New York. Raven Press, Ltd,. 849–895, 1991.
Stinski, *J. Virol.* 26:686–701, 1978.
Toyoshima and Hunter, *Cell*, 78:67–74, 1994.
van den Heuvel and Harlow, *Science*, 262:2050–2054, 1993.
Vesely et al., *Eur. J. Biochem.*, 224:771–786, 1994.
Villar et al., *Am. J. Med.*, 76:924–928, 1984.
Wade et al., *Mol. Cell. Biol.*, 12:4364–4374, 1992.
Weinberg, *Cell* 81:323–330, 1995.
Weller and Hanshaw, *N. Engl. J. Med.*, 266:1233–1244, 1964.
Weller, *N Engl. J. Med.*, 285:267–274, 1971.
Xiong et al., *Cell*, 71:505–514, 1992.
Yurochko et al,. *J. Virol.* 69:5391–5400, 1995.
Zhang et al., *Genes Dev.*, 8:1750–1758, 1994.
Zhang et al., *Mol. Biol. Cell.*, 4:897–906, 1993.

What is claimed is:

1. A method for inhibiting proliferation of a mammalian DNA virus, the method comprising administering a prophylactically or therapeutically effective amount of a Cdk inhibitor to a patient or animal exposed to or infected by said virus.

2. The method of claim 1, further defined as a method for killing cells infected by a DNA virus, comprising administering a cytotoxically effective amount of the Cdk inhibitor to an animal or human patient with said infected cells.

3. The method of claim 1, where the Cdk is Cdk2.

4. The method of claim 1 where the DNA virus is a cytomegalovirus.

5. The method of claim 1 where the DNA virus is HCMV.

6. The method of claim 1, further defined as a method for inhibiting replication of a DNA virus, comprising administering a prophylactically or therapeutically effective amount of roscovitine to a patient exposed to or infected by said virus.

7. The method of claim 4, further defined as a method for treating an animal for infection with a cytomegalovirus.

8. The method of claim 7 where the Cdk is Cdk2.

9. A method for treating a patient infected with human cytomegalovirus, the method comprising parenterally administering a therapeutically effective amount of roscovitine and/or olomoucine to the infected patient.

10. The method of claim 1 where the Cdk is cyclin E/Cdk2.

11. The method of claim 1 where the administering is parenteral.

12. The method of claim 1 where the Cdk inhibitor is roscovitine.

13. The method of claim 12 where the therapeutically or prophylactically effective amount is from about 0.1 µg/kg to about 1000 µg/kg.

14. The method of claim 12 where the therapeutically effective amount is from about 0.1 to about 100 µg/kg.

15. The method of claim 1 where the Cdk inhibitor is olomoucine.

16. The method of claim 15 where the therapeutically or prophylactically effective amount is from about 10 µg/kg to about 1000 µg/kg.

17. The method of claim 1 where the DNA virus is a herpesvirus.

18. The method of claim 1 where the DNA virus is a papovirus.

19. The method of claim 1 where the DNA virus is an adenovirus.

20. The method of claim 1 where the DNA virus is Herpes simplex.

21. The method of claim 1 where the administration is topical or intracavitary.

22. The method of claim 1 where the amount is sufficient to result in about a 4 µM to about 20 µM concentration in the environment of cells infected or potentially infected with a virus.

23. The method of claim 9 where roscovitine is administered.

24. The method of claim 23 where the therapeutically effective amount is from about 0.1 µg/kg to about 1000 µpg/kg.

25. The method of claim 23 where the therapeutically effective amount is from about 0.1 to about 100 µg/kg.

26. The method of claim 9 where olomoucine is administered.

27. The method of claim 26 where the therapeutically effective amount is from about 10 µg/kg to about 1000 µg/kg.

* * * * *

UNITED STATES PATENT AND TRADEMARK OFFICE
CERTIFICATE OF CORRECTION

PATENT NO. : 6,486,166 B1  Page 1 of 1
DATED : November 26, 2002
INVENTOR(S) : Thomas Albrecht et al.

It is certified that error appears in the above-identified patent and that said Letters Patent is hereby corrected as shown below:

Column 33,
Line 26, please insert -- the -- before "proliferation"

Column 34,
Line 39, please delete "µpg/kg" and insert -- µg/kg -- therefor.

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,486,166 B1
DATED : November 26, 2002
INVENTOR(S) : Albrecht et al.

It is certified that error appears in the above-identified patent and that said Letters Patent is hereby corrected as shown below:

<u>Title page,</u>
Item [73], please delete "Board of Regents, The University of Texas" and insert
-- Board of Regents, The University of Texas Systems -- therefor.

Signed and Sealed this

Seventeenth Day of June, 2003

JAMES E. ROGAN
*Director of the United States Patent and Trademark Office*